(12) United States Patent
Kubota et al.

(10) Patent No.: US 12,279,522 B2
(45) Date of Patent: Apr. 15, 2025

(54) PHOTOELECTRIC CONVERSION DEVICE AND OPTICAL FUNCTIONAL DEVICE

(71) Applicant: SEMICONDUCTOR ENERGY LABORATORY CO., LTD., Atsugi (JP)

(72) Inventors: Daisuke Kubota, Kanagawa (JP); Taisuke Kamada, Saitama (JP); Yasuhiro Niikura, Tokyo (JP); Ryo Hatsumi, Kanagawa (JP); Akio Yamashita, Kanagawa (JP); Sachiko Kawakami, Kanagawa (JP); Anna Tada, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 538 days.

(21) Appl. No.: 17/727,158

(22) Filed: Apr. 22, 2022

(65) Prior Publication Data

US 2022/0376182 A1 Nov. 24, 2022

(30) Foreign Application Priority Data

Apr. 30, 2021 (JP) .................................. 2021-077640
Jun. 4, 2021 (JP) .................................. 2021-094340

(51) Int. Cl.
*H10K 85/30* (2023.01)
*C07D 209/82* (2006.01)
(Continued)

(52) U.S. Cl.
CPC ......... *H10K 85/621* (2023.02); *C07D 209/82* (2013.01); *C07D 219/16* (2013.01); *C07D 221/20* (2013.01); *C07D 307/91* (2013.01); *C07D 333/76* (2013.01); *C07D 401/04* (2013.01); *C07D 401/06* (2013.01);
(Continued)

(58) Field of Classification Search
CPC ............. H10K 30/00–89; H10K 65/00; H10K 85/621; H10K 85/624
See application file for complete search history.

(56) References Cited

U.S. PATENT DOCUMENTS 8,736,587 B2 5/2014 Yamazaki
9,817,520 B2 11/2017 Ikeda et al.
(Continued)

FOREIGN PATENT DOCUMENTS

CN 107209610 A 9/2017
EP 3259656 A 12/2017
(Continued)

*Primary Examiner* — Daniel P Shook
(74) *Attorney, Agent, or Firm* — Fish & Richardson P.C.

(57) ABSTRACT

To provide a novel photoelectric conversion device that is highly convenient, useful, or reliable. The photoelectric conversion device includes a first electrode, a second electrode, and a first unit. The first unit is located between the first electrode and the second electrode. The first unit contains a first electron-donating material and a first electron-accepting material. The first electron-donating material is a condensed aromatic compound, and the first electron-accepting material has a perylene skeleton and two or more alkyl groups. The alkyl groups each independently have 1 to 13 carbon atoms.

19 Claims, 20 Drawing Sheets

(51) Int. Cl.

| | |
|---|---|
| *C07D 219/16* | (2006.01) |
| *C07D 221/20* | (2006.01) |
| *C07D 307/91* | (2006.01) |
| *C07D 333/76* | (2006.01) |
| *C07D 401/04* | (2006.01) |
| *C07D 401/06* | (2006.01) |
| *C07D 403/10* | (2006.01) |
| *C07D 405/04* | (2006.01) |
| *C07D 409/10* | (2006.01) |
| *C07D 413/10* | (2006.01) |
| *C07D 519/00* | (2006.01) |
| *C07F 7/22* | (2006.01) |
| *C07F 15/00* | (2006.01) |
| *H10K 30/20* | (2023.01) |
| *H10K 50/16* | (2023.01) |
| *H10K 65/00* | (2023.01) |
| *H10K 85/60* | (2023.01) |

(52) U.S. Cl.
CPC ......... *C07D 403/10* (2013.01); *C07D 405/04* (2013.01); *C07D 409/10* (2013.01); *C07D 413/10* (2013.01); *C07D 519/00* (2013.01); *C07F 7/2284* (2013.01); *C07F 15/0093* (2013.01); *H10K 50/16* (2023.02); *H10K 85/30* (2023.02); *H10K 85/622* (2023.02); *H10K 85/625* (2023.02); *H10K 85/6572* (2023.02); *H10K 85/6574* (2023.02); *H10K 85/6576* (2023.02); *H10K 30/20* (2023.02); *H10K 65/00* (2023.02)

(56) References Cited

U.S. PATENT DOCUMENTS

| | | |
|---|---|---|
| 10,431,164 B2 | 10/2019 | Okamoto |
| 10,769,990 B2 | 9/2020 | Cho et al. |
| 2005/0007353 A1 | 1/2005 | Smith et al. |
| 2008/0223444 A1* | 9/2008 | Marder ................ C09B 57/008 546/37 |
| 2008/0297487 A1 | 12/2008 | Hotelling et al. |
| 2010/0007632 A1 | 1/2010 | Yamazaki |
| 2010/0141601 A1 | 6/2010 | Kim et al. |
| 2011/0043473 A1 | 2/2011 | Kozuma |
| 2013/0009909 A1 | 1/2013 | Yamazaki et al. |
| 2014/0299879 A1 | 10/2014 | Yamazaki |
| 2014/0340363 A1 | 11/2014 | Ikeda et al. |
| 2016/0246396 A1 | 8/2016 | Dickinson. et al. |
| 2017/0125704 A1 | 5/2017 | Suzuki et al. |
| 2017/0365224 A1 | 12/2017 | Okamoto |
| 2018/0157361 A1 | 6/2018 | Kim |
| 2019/0163313 A1 | 5/2019 | Kim |
| 2021/0043840 A1 | 2/2021 | Seo et al. |
| 2021/0264128 A1 | 8/2021 | Feng et al. |
| 2022/0068181 A1 | 3/2022 | Watanabe et al. |

FOREIGN PATENT DOCUMENTS

| | | |
|---|---|---|
| JP | 2008-286905 A | 11/2008 |
| JP | 2015-005280 A | 1/2015 |
| JP | 2015-026387 A | 2/2015 |
| JP | 2016-192209 A | 11/2016 |
| JP | 2017-227896 A | 12/2017 |
| JP | 2018-506124 | 3/2018 |
| KR | 2013-0006295 A | 1/2013 |
| KR | 10-1535131 | 7/2015 |
| TW | 201308166 | 2/2013 |
| WO | WO-2016/133602 | 8/2016 |
| WO | WO-2020/152556 | 7/2020 |

\* cited by examiner

PHOTOELECTRIC CONVERSION DEVICE AND OPTICAL FUNCTIONAL DEVICE

BACKGROUND OF THE INVENTION

1. Field of the Invention

One embodiment of the present invention relates to a photoelectric conversion device, an optical functional device, or a semiconductor device.

Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specific examples of the technical field of one embodiment of the present invention disclosed in this specification include a semiconductor device, a display device, a light-emitting apparatus, a power storage device, a memory device, a method for driving any of them, and a method for manufacturing any of them.

2. Description of the Related Art

A functional panel in which a pixel provided in a display region includes a light-emitting element and a photoelectric conversion element is known (Patent Document 1). An example is a functional panel including a first driver circuit, a second driver circuit, and a region, in which the first driver circuit supplies a first selection signal, the second driver circuit supplies a second selection signal and a third selection signal, and the region includes a pixel. The pixel includes a first pixel circuit, a light-emitting element, a second pixel circuit, and a photoelectric conversion element. The first pixel circuit is supplied with the first selection signal, the first pixel circuit obtains an image signal on the basis of the first selection signal, the light-emitting element is electrically connected to the first pixel circuit, and the light-emitting element emits light on the basis of the image signal. The second pixel circuit is supplied with the second selection signal and the third selection signal in a period during which the first selection signal is not supplied, the second pixel circuit obtains an imaging signal on the basis of the second selection signal and supplies the imaging signal on the basis of the third selection signal, and the photoelectric conversion element is electrically connected to the second pixel circuit and generates the imaging signal.

REFERENCE

[Patent Document 1] PCT International Publication No. WO2020/152556

SUMMARY OF THE INVENTION

An object of one embodiment of the present invention is to provide a novel photoelectric conversion device that is highly convenient, useful, or reliable. Another object is to provide a novel optical functional device that is highly convenient, useful, or reliable. Another object is to provide a novel photoelectric conversion device, a novel optical functional device, or a novel semiconductor device.

Note that the description of these objects does not preclude the existence of other objects. One embodiment of the present invention does not need to achieve all the objects listed above. Other objects will be apparent from and can be derived from the description of the specification, the drawings, the claims, and the like.

(1) One embodiment of the present invention is a photoelectric conversion device including a first electrode, a second electrode, and a first unit.

The first unit is located between the first electrode and the second electrode, and the first unit contains a first electron-donating material and a first electron-accepting material.

The first electron-donating material is a condensed aromatic compound, and the first electron-accepting material has a perylene skeleton and two or more alkyl groups. The alkyl groups each independently have carbon atoms whose number is greater than or equal to 1 and less than or equal to 13.

(2) Another embodiment of the present invention is the above photoelectric conversion device in which the first unit exhibits a local maximum at a wavelength of less than 500 nm and an absorption edge at a wavelength of greater than or equal to 500 nm in an absorption spectrum.

This allows incident light in the visible light region to be captured and converted into an electric signal. In addition, an object that reflects light in the visible light region can be sensed and the light reflected by the object can be converted into an electric signal. As a result, a novel photoelectric conversion device that is highly convenient, useful, or reliable can be provided.

(3) Another embodiment of the present invention is the photoelectric conversion device in which the first electron-donating material is a condensed aromatic compound having condensed rings whose number is greater than or equal to 4 and less than or equal to 11.

This allows improvement in current saturation characteristics or conversion of light into a current with high efficiency. In addition, a continuous change in the intensity of incident light can be sensed and converted into an electric signal. The photoelectric conversion device can be suitably used for an imaging device. As a result, a novel photoelectric conversion device that is highly convenient, useful, or reliable can be provided.

(4) Another embodiment of the present invention is the photoelectric conversion device in which the alkyl groups each have a branched structure.

This can increase the solubility of the first electron-accepting material. In addition, purity measurement is facilitated. In addition, sublimation purification of the first electron-accepting material is facilitated. In addition, evaporation is facilitated. In addition, the quality management of the electron-accepting material is facilitated. As a result, a novel photoelectric conversion device that is highly convenient, useful, or reliable can be provided.

(5) Another embodiment of the present invention is the photoelectric conversion device in which the first electron-accepting material is a perylenetetracarboxylic diimide derivative expressed by General Formula (R0).

[Chemical Formula 1]

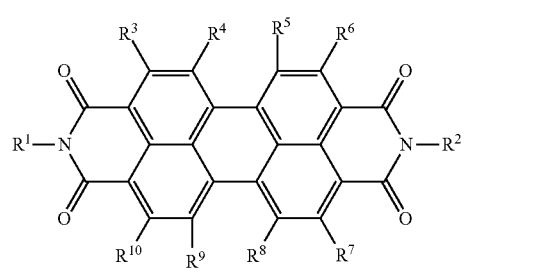

(R0)

In General Formula (R0), $R^1$ and $R^2$ each independently represent hydrogen, a chain alkyl group having 1 to 13 carbon atoms, or a branched alkyl group having 3 to 13 carbon atoms, and $R^3$ to $R^{10}$ each independently represent hydrogen, a chain alkyl group having 1 to 13 carbon atoms, a branched alkyl group having 3 to 13 carbon atoms, a halogenated alkyl group having 1 to 13 carbon atoms, a cycloalkyl group having 3 to 13 carbon atoms, or halogen.

(6) Another embodiment of the present invention is the photoelectric conversion device including the first layer.

The first layer is located between the first electrode and the first unit and contains a second electron-accepting material. In addition, the first layer has an electrical resistivity greater than or equal to $1 \times 10^2$ Ω·cm and less than or equal to $1 \times 10^8$ Ω·cm.

(7) Another embodiment of the present invention is the photoelectric conversion device including a second layer.

The second layer is located between the first unit and the second electrode and contains a second electron-donating material.

(8) Another embodiment of the present invention is the photoelectric conversion device in which the first unit includes a third layer, a fourth layer, and a fifth layer.

The third layer is located between the fourth layer and the fifth layer and contains the first electron-accepting material and the first electron-donating material.

The fourth layer is located between the first electrode and the third layer and contains a hole-transport material.

The fifth layer is located between the third layer and the second electrode and contains an electron-transport material.

(9) Another embodiment of the present invention is an optical functional device including the above photoelectric conversion device and a light-emitting device, in which the light-emitting device is adjacent to the photoelectric conversion device.

(10) Another embodiment of the present invention is an optical functional device including the above photoelectric conversion device and a light-emitting device.

The light-emitting device is adjacent to the photoelectric conversion device and includes a second unit, a third electrode, and the second electrode.

The second unit is located between the third electrode and the second electrode and includes a sixth layer, the fourth layer, and the fifth layer.

The fourth layer is located between the third electrode and the sixth layer, and the fifth layer is located between the sixth layer and the second electrode. The sixth layer contains a light-emitting material.

Although the block diagram in drawings attached to this specification shows components classified based on their functions in independent blocks, it is difficult to classify actual components based on their functions completely, and one component can have a plurality of functions.

According to one embodiment of the present invention, a novel photoelectric conversion device that is highly convenient, useful, or reliable can be provided. A novel optical functional device that is highly convenient, useful, or reliable can be provided. A novel photoelectric conversion device, a novel optical functional device, or a novel semiconductor device can be provided.

Note that the description of these effects does not preclude the existence of other effects. One embodiment of the present invention does not need to have all the effects listed above. Other effects will be apparent from and can be derived from the description of the specification, the drawings, the claims, and the like.

DETAILED DESCRIPTION OF THE INVENTION

Figure 1A:
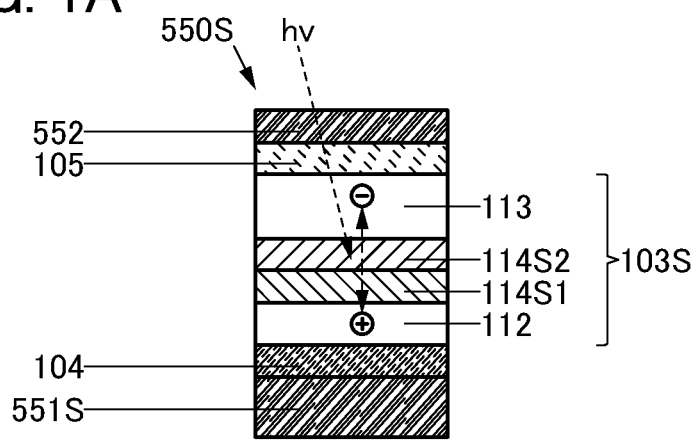
FIGS. 1A and 1B illustrate a structure of a photoelectric conversion device of an embodiment of the present invention.

A photoelectric conversion device includes a first electrode, a second electrode, and a first unit. The first unit is located between the first electrode and the second electrode and contains a first electron-donating material and a first electron-accepting material. The first electron-donating material is a condensed aromatic compound, and the first electron-accepting material has a perylene skeleton and two or more alkyl groups. The alkyl groups each independently have carbon atoms whose number is greater than or equal to 1 and less than or equal to 13.

Thus, current saturation characteristics can be improved. Light can be converted into a current with high efficiency. In addition, a continuous change in the intensity of incident light can be sensed and converted into an electric signal. The photoelectric conversion device can be suitably used for an imaging device. As a result, a novel photoelectric conversion device that is highly convenient, useful, or reliable can be provided.

Embodiments will be described in detail with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments. Note that in structures of the invention described below, the same portions or portions having similar functions are denoted by the same reference numerals in different drawings, and the description thereof is not repeated.

Embodiment 1

In this embodiment, a structure of a photoelectric conversion device 550S of one embodiment of the present invention will be described with reference to FIGS. 1A and 1B.

Figure 1B:
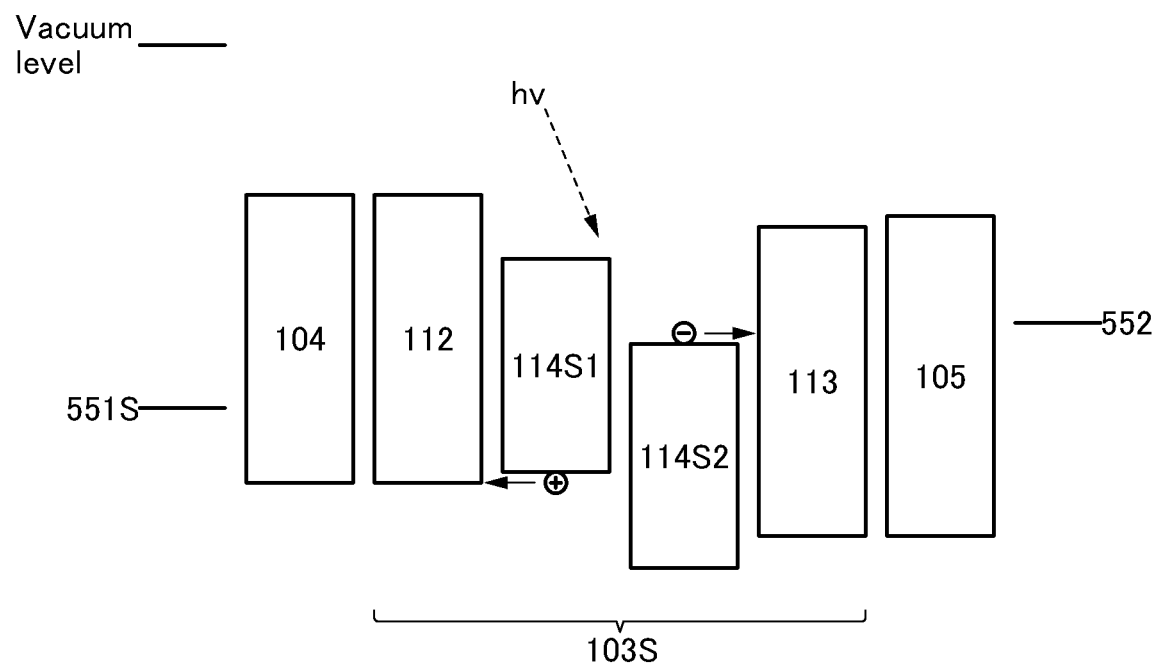

FIG. 1A is a cross-sectional view of the photoelectric conversion device 550S of one embodiment of the present invention, and FIG. 1B illustrates a structure of a unit 103S of the photoelectric conversion device 550S of one embodiment of the present invention. FIG. 1B is an energy diagram of an electrode 551S, a layer 104, the unit 103S (a layer 112, a layer 114S1, a layer 114S2, and a layer 113), a layer 105, and an electrode 552. Solid lines indicate vacuum levels.

<Structure Example 1 of Photoelectric Conversion Device 550S>

The photoelectric conversion device 550S described in this embodiment includes the electrode 551S, the electrode 552, and the unit 103S (see FIG. 1A). The unit 103S is located between the electrode 551S and the electrode 552.

«Structure Example 1 of Unit 103S»

The unit 103S contains an electron-donating material DM1 (first material) and an electron-accepting material AM1 (second material). «Structure Example 2 of Unit 103S»

The unit 103S exhibits a local maximum at a wavelength of less than 500 nm and an absorption edge at a wavelength of greater than or equal to 500 nm in the absorption spectrum. For example, a material whose local maximum is at a wavelength of less than 500 nm and whose absorption edge is at a wavelength of greater than or equal to 500 nm can be used as the electron-donating material DM1. A material whose local maximum is at a wavelength of less than 500 nm and whose absorption edge is at a wavelength of greater than or equal to 500 nm can be used as the electron-accepting material AM1. A mixed material whose local maximum is at a wavelength of less than 500 nm and whose absorption edge is at a wavelength of greater than or equal to 500 nm can be used as a mixed material of the electron-donating material DM1 and the electron-accepting material AM1.

Thus, incident light hv in the visible light region can be captured and converted into an electric signal. In addition, an object that reflects light in the visible light region can be sensed and the light reflected by the object can be converted into an electric signal. As a result, a novel photoelectric conversion device that is highly convenient, useful, or reliable can be provided.

[Structure Example of Electron-Donating Material DM1]

The electron-donating material DM1 is a condensed aromatic compound. For example, a condensed aromatic compound having condensed rings whose number is greater than or equal to 4 and less than or equal to 11 can be used as the electron-donating material DM1. An element included in an aromatic ring is not limited to carbon and may include nitrogen.

Specifically, a tetracene derivative, a pentacene derivative, a periflanthene derivative, or the like can be used. For example, the condensed aromatic compounds shown below, such as tetraphenyldibenzoperiflanthene (abbreviation: DBP) and rubrene, can be used for the electron-donating material DM1.

[Chemical Formulae 2]

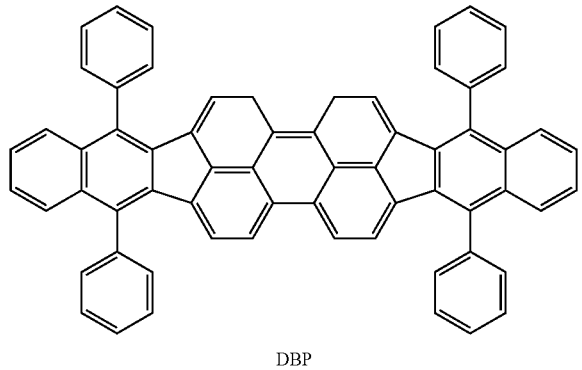

DBP

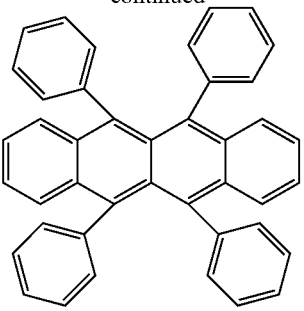

Rubrene

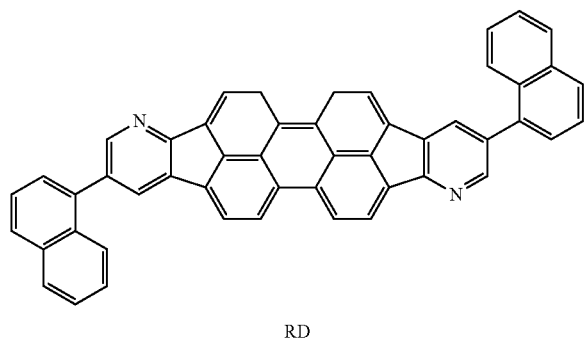

RD

[Structure Example 1 of Electron-Accepting Material AM1]

The electron-accepting material AM1 has a perylene skeleton and 2 or more alkyl groups. It is preferable that the alkyl groups each independently have carbon atoms whose number is greater than or equal to 1 and less than or equal to 13. In terms of quantum efficiency, the number of carbon atoms is preferably less than or equal to 12, further preferably less than or equal to 10, still further preferably less than or equal to 6.

Thus, current saturation characteristics can be improved. Light can be converted into a current with high efficiency. In addition, a continuous change in the intensity of incident light can be sensed and converted into an electric signal. The photoelectric conversion device can be suitably used for an imaging device. As a result, a novel photoelectric conversion device that is highly convenient, useful, or reliable can be provided.

The unit 103S includes the electron-donating material DM1 and the electron-accepting material AM1 and can also be referred to as an active layer. The unit 103S absorbs light, and charge separation is induced by photoexcitation energy hv in the unit 103S that has absorbed light (see FIGS. 1A and 1B). Then, holes are trapped to the electron-donating material DM1 side and electrons are trapped to the electron-accepting material AM1 side. For example, in the case where a stack of the layer 114S1 containing the electron-donating material DM1 and the layer 114S2 containing the electron-accepting material AM1 is used, holes indicated by a positive sign (+) in FIGS. 1A and 1B move on the layer 114S1 side, and electrons indicated by a negative sign (−) in FIGS. 1A and 1B move on the layer 114S2 side (see FIG. 1B). Accordingly, the photoelectric conversion device can convert light into a current. It is preferable that the highest occupied molecular orbital (HOMO) level of the electron-donating material DM1 be higher than the HOMO level of the electron-accepting material AM1 and the lowest unoccupied molecular orbital (LUMO) level of the electron-donating material DM1 be higher than the LUMO level of the electron-accepting material AM1. For example, when the electron-donating material DM1 is used for the layer 114S1 and the electron-accepting material AM1 is used for the layer 114S2, the energy diagram shown in FIG. 1B is obtained.

[Structure Example 2 of Electron-Accepting Material AM1]

The electron-accepting material AM1 having a branched alkyl group is suitable for the photoelectric conversion device. It is particularly preferable that the branched alkyl group have carbon atoms whose number is greater than or equal to 3 and less than or equal to 12. In terms of quantum efficiency, the number of carbon atoms is preferably less than or equal to 10, particularly preferably less than or equal to 6.

In that case, the solubility of the electron-accepting material AM1 can be increased. Furthermore, quality management of the electron-accepting material AM1 is facilitated. As a result, a novel photoelectric conversion device that is highly convenient, useful, or reliable can be provided.

[Structure Example 3 of Electron-Accepting Material AM1]

For example, a perylenetetracarboxylic diimide derivative expressed by General Formula (R0) can be suitably used as the electron-accepting material AM1.

[Chemical Formula 3]

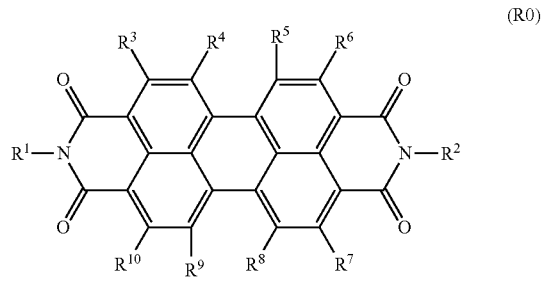

(R0)

In General Formula (R0), $R^1$ and $R^2$ each independently represent hydrogen, a chain alkyl group having 1 to 13 carbon atoms, or a branched alkyl group having 3 to 13 carbon atoms, and $R^3$ to $R^{10}$ each independently represent hydrogen, a chain alkyl group having 1 to 13 carbon atoms, a branched alkyl group having 3 to 13 carbon atoms, a halogenated alkyl group having 1 to 13 carbon atoms, a cycloalkyl group having 3 to 13 carbon atoms, or halogen. It is particularly preferable that $R^1$ and $R^2$ each independently represent a chain alkyl group having 2 to 12 carbon atoms so that high solubility can be obtained. It is further preferable that $R^1$ and $R^2$ each independently represent a branched alkyl group.

Specifically, N,N'-dimethyl-3,4,9,10-perylenetetracarboxylic diimide (abbreviation: Me-PTCDI), N,N'-di-n-octyl-3,4,9,10-perylenetetracarboxylic diimide (abbreviation: PTCDI-C8), N,N'-ditridecylperylene-3,4,9,10-tetracarboxylic diimide (abbreviation: PTCDI-C13), N,N'-bis(2-ethylhexyl)-3,4,9,10-perylenetetracarboxylic diimide (abbreviation: EtHex-PTCDI), or the like shown below can be used as the electron-accepting material AM1.

[Chemical Formulae 4]

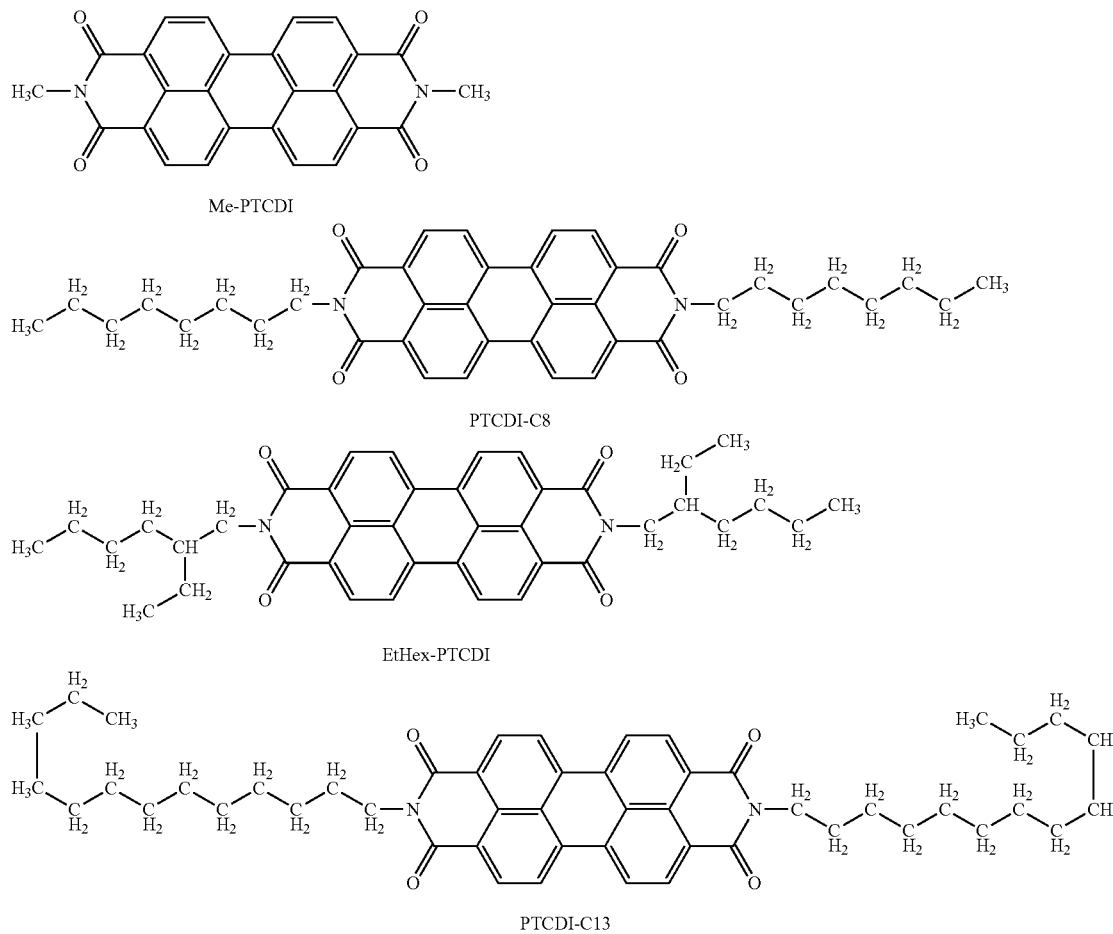

<Structure Example 2 of Photoelectric Conversion Device 550S>

The photoelectric conversion device 550S described in this embodiment includes the electrode 551S and the layer 104 (see FIG. 1A). The layer 104 is located between the electrode 551S and the unit 103S.

<Structure Example of Electrode 551S>

For example, a conductive material can be used for the electrode 551S. Specifically, a single layer or a stack using a metal, an alloy, or a film containing a conductive compound can be used for the electrode 551S.

A film that efficiently reflects light can be used for the electrode 551S, for example. Specifically, an alloy containing silver, copper, and the like, an alloy containing silver, palladium, and the like, or a metal film of aluminum or the like can be used for the electrode 551S.

A film having a visible-light-transmitting property can be used for the electrode 551S, for example. Specifically, a single layer or a stack using a metal film, an alloy film, a conductive oxide film, or the like that is thin enough to transmit light can be used for the electrode 551S.

For example, a conductive oxide containing indium can be used. Specifically, indium oxide, indium oxide-tin oxide (abbreviation: ITO), indium oxide-tin oxide containing silicon or silicon oxide (abbreviation: ITSO), indium oxide-zinc oxide, indium oxide containing tungsten oxide and zinc oxide (abbreviation: IWZO), or the like can be used.

For another example, a conductive oxide containing zinc can be used. Specifically, zinc oxide, zinc oxide to which gallium is added, zinc oxide to which aluminum is added, or the like can be used.

For another example, gold (Au), platinum (Pt), nickel (Ni), tungsten (W), chromium (Cr), molybdenum (Mo), iron (Fe), cobalt (Co), copper (Cu), palladium (Pd), a nitride of a metal material (e.g., titanium nitride), or the like can be used. Graphene can also be used.

«Structure Example of Layer 104»

A hole-injection material can be used for the layer 104, for example.

Specifically, an electron-accepting substance can be used for the layer 104. Alternatively, a composite material containing a plurality of kinds of substances can be used for the layer 104.

[Electron-Accepting Substance]

An organic compound or an inorganic compound can be used as the electron-accepting substance.

For example, a compound having an electron-withdrawing group (a halogen or cyano group) can be used as the electron-accepting substance. An electron-accepting organic compound is easily evaporated, which facilitates film deposition. Thus, the productivity of the photoelectric conversion device can be increased.

Specifically, 7,7,8,8-tetracyano-2,3,5,6-tetrafluoroquinodimethane (abbreviation: $F_4$-TCNQ), chloranil, 2,3,6,7, 10,11-hexacyano-1,4,5,8,9,12-hexaazatriphenylene (abbreviation: HAT-CN), 1,3,4,5,7,8-hexafluorotetracyanonaphthoquinodimethane (abbreviation: F6-TCNNQ), 2-(7-dicyanomethylene-1,3,4,5,6,8,9,10-octafluoro-7H-pyren-2-ylidene)malononitrile, or the like can be used.

A compound in which electron-withdrawing groups are bonded to a condensed aromatic ring having a plurality of heteroatoms, such as HAT-CN, is particularly preferable because it is thermally stable.

A [3]radialene derivative having an electron-withdrawing group (in particular, a cyano group or a halogen group such as a fluoro group) has a very high electron-accepting property and thus is preferred.

Specifically, α,α',α"-1,2,3-cyclopropanetriylidenetris[4-cyano-2,3,5,6-tetrafluorobenzeneacetonitrile], α,α',α"-1,2,3-cyclopropanetriylidenetris [2,6-dichloro-3,5-difluoro-4-(trifluoromethyl)benzeneacetonitrile], α,α',α"-1,2,3-cyclopropanetriylidenetris[2,3,4,5,6-pentafluorobenzeneacetonitrile], or the like can be used.

For the electron-accepting substance, a molybdenum oxide, a vanadium oxide, a ruthenium oxide, a tungsten oxide, a manganese oxide, or the like can be used.

It is possible to use any of the following materials: phthalocyanine-based complex compounds such as phthalocyanine (abbreviation: H$_2$Pc) and copper phthalocyanine (abbreviation: CuPc); and compounds each having an aromatic amine skeleton such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD).

In addition, high molecular compounds such as poly(3,4-ethylenedioxythiophene)/poly(styrenesulfonic acid) (abbreviation: PEDOT/PSS), and the like can be used.

«Structure Example of Layer 104»

The layer 104 contains an electron-accepting material AM2. The layer 104 has an electrical resistivity greater than or equal to $1\times10^2$ [Ω·cm] and less than or equal to $1\times10^8$ [Ω·cm].

[Structure Example 1 of Composite Material]

For example, a composite material containing an electron-accepting substance and a hole-transport material can be used for the layer 104.

For the hole-transport material in the composite material, for example, a compound having an aromatic amine skeleton, a carbazole derivative, an aromatic hydrocarbon, an aromatic hydrocarbon having a vinyl group, or a high molecular compound (such as an oligomer, a dendrimer, or a polymer) can be used. A material having a hole mobility of $1\times10^{-6}$ cm$^2$/Vs or higher can be suitably used as the hole-transport material in the composite material.

A substance having a relatively deep HOMO level can be suitably used for the hole-transport material in the composite material.

As a compound having an aromatic amine skeleton, for example, N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), {4-[bis(3-methylphenyl)amino]phenyl}-N,N'-diphenyl-(1,1'-biphenyl)-4,4'-diamine (abbreviation: DNTPD), or 1,3,5-tris[N-(4-diphenylaminophenyl)-N-phenylamino]benzene (abbreviation: DPA3B) can be used.

As a carbazole derivative, for example, 3-[N-(9-phenylcarbazol-3-yl)-N-phenyl amino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), or 1,4-bis[4-(N-carbazolyl)phenyl]-2,3,5,6-tetraphenylbenzene can be used.

As an aromatic hydrocarbon, for example, 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, or coronene can be used.

As an aromatic hydrocarbon having a vinyl skeleton, for example, 4,4'-bis(2,2-diphenylvinyl)biphenyl (abbreviation: DPVBi), or 9,10-bis[4-(2,2-diphenylvinyl)phenyl]anthracene (abbreviation: DPVPA) can be used.

As a high molecular compound, for example, poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: Poly-TPD) can be used.

Furthermore, a substance having any of a carbazole skeleton, a dibenzofuran skeleton, a dibenzothiophene skeleton, and an anthracene skeleton can be suitably used as the hole-transport material in the composite material, for example. Moreover, a substance including any of the following can be used as the hole-transport material in the composite material: an aromatic amine having a substituent that includes a dibenzofuran ring or a dibenzothiophene ring, an aromatic monoamine that includes a naphthalene ring, and an aromatic monoamine in which a 9-fluorenyl group is bonded to nitrogen of amine through an arylene group.

Examples of the hole-transport material in the composite material include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho [1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl) triphenylamine (abbreviation: BBAαNβNB-03), 4,4'- diphenyl-4"-(7-phenyl)naphthyl-2-yltriphenylamine (abbreviation: BBAPβNB-03), 4,4'-diphenyl-4"-(6;2'-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNaNB), 4,4'-diphenyl-4"-(5;2'-binaphthyl-1-yl)triphenylamine (abbreviation: BBAβNaNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi(9H-fluoren)-2-amine (abbreviation: PCBNBSF), N,N-bis([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N4-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

<Structure Example 3 of Photoelectric Conversion Device 550S>

The photoelectric conversion device 550S described in this embodiment includes the layer 105 (see FIG. 1A). The layer 105 is located between the unit 103S and the electrode 552.

<Structure Example of Electrode 552>

For example, a conductive material can be used for the electrode 552. Specifically, a single layer or a stack using a metal, an alloy, or a material containing a conductive compound can be used for the electrode 552.

For example, a material that can be used for the electrode 551S can be used for the electrode 552.

For example, an element belonging to Group 1 or Group 2 of the periodic table, a rare earth metal, or an alloy containing any of these elements can be used for the electrode 552.

Specifically, lithium (Li), cesium (Cs), or the like; magnesium (Mg), calcium (Ca), strontium (Sr), or the like; europium (Eu), ytterbium (Yb), or the like; or an alloy containing any of these (MgAg or AlLi) can be used for the electrode 552.

«Structure Example of Layer 105»

For example, an electron-injection material can be used for the layer 105.

Specifically, an electron-donating substance can be used for the layer 105. Alternatively, a material in which an electron-donating substance and an electron-transport material are combined can be used for the layer 105. Alternatively, an electride can be used for the layer 105.

«Structure Example of Layer 105»

The layer 105 includes an electron-donating material DM2. An electron-donating substance can be used as the electron-donating material DM2.

[Electron-Donating Substance]

For example, an alkali metal, an alkaline earth metal, a rare earth metal, or a compound thereof (an oxide, a halide, a carbonate, or the like) can be used as the electron-donating substance. Alternatively, an organic compound such as tetrathianaphthacene (abbreviation: TTN), nickelocene, or decamethylnickelocene can be used as the electron-donating substance.

As an alkali metal compound (including an oxide, a halide, and a carbonate), lithium oxide, lithium fluoride (LiF), cesium fluoride (CsF), lithium carbonate, cesium carbonate, 8-hydroxyquinolinato-lithium (abbreviation: Liq), or the like can be used.

As an alkaline earth metal compound (including an oxide, a halide, and a carbonate), calcium fluoride ($CaF_2$) or the like can be used.

[Structure Example 1 of Composite Material]

A composite material of two or more kinds of substances can be used as the electron-injection material. For example, an electron-donating substance and an electron-transport material can be used for the composite material.

[Electron-Transport Material]

For example, a metal complex or an organic compound having a π-electron deficient heteroaromatic ring skeleton can be used as the electron-transport material.

A material having an electron mobility higher than or equal to $1\times10^{-7}$ $cm^2/Vs$ and lower than or equal to $5\times10^{-5}$ $cm^2/Vs$ when the square root of the electric field strength [V/cm] is 600 can be suitably used as the electron-transport material. In this case, the electron-transport property in the electron-transport layer can be suppressed. The amount of electrons injected into the light-emitting layer can be controlled. The light-emitting layer can be prevented from having excess electrons.

As a metal complex, bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ) can be used, for example.

As an organic compound having a π-electron deficient heteroaromatic ring skeleton, a heterocyclic compound having a polyazole skeleton, a heterocyclic compound having a diazine skeleton, a heterocyclic compound having a pyridine skeleton, a heterocyclic compound having a triazine skeleton, or the like can be used, for example. In particular, the heterocyclic compound having a diazine skeleton and the heterocyclic compound having a pyridine skeleton have favorable reliability and thus are preferable. In addition, the heterocyclic compound having a diazine (pyrimidine or pyrazine) skeleton has a high electron-transport property.

As a heterocyclic compound having a polyazole skeleton, 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II) can be used, for example.

As a heterocyclic compound having a diazine skeleton, 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), or 4,8-bis[3-(dibenzothiophen-4-yl)phenyl]benzo[h]quinazoline (abbreviation: 4,8mDBtP2Bqn) can be used, for example.

As a heterocyclic compound having a pyridine skeleton, 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB) can be used, for example.

As a heterocyclic compound having a triazine skeleton, 2-[3'-(9,9-dimethyl-9H-fluoren-2-yl)biphenyl-3-yl]-4,6-diphenyl-1,3,5-triazine (abbreviation: mFBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2-{3-[3-(benzo[b]naphtho[1,2-d]furan-8-yl)phenyl]phenyl}-4,6-diphenyl-1,3,5-triazine (abbreviation: mBnfBPTzn), or 2-{3-[3-(benzo[b]naphtho[1,2-d]furan-6-yl)phenyl]phenyl}-4,6-diphenyl-1,3,5-triazine (abbreviation: mBnfBPTzn-02) can be used, for example.

«Structure Example 3 of unit 103S»

For example, a mixed material containing the electron-donating material DM1 and the electron-accepting material AM1 can be used for the unit 103S. A structure using such a mixed material containing the electron-donating material DM1 and the electron-accepting material AM1 can be referred to as a bulk heterojunction structure.

«Structure Example 4 of Unit 103S»

A stacked-layer structure in which a layer containing the electron-donating material DM1 and a layer containing the electron-accepting material AM1 are stacked can be used for the unit 103S. The structure in which the layer containing the electron-donating donating material DM1 and the layer containing the electron-accepting material AM1 are stacked can be referred to as a heterojunction structure.

For example, a layer 114S including the layer 114S1 and the layer 114S2 can be used for the unit 103S (see FIG. 1A). Specifically, the electron-donating material DM1 can be used for the layer 114S1, and the electron-accepting material AM1 can be used for the layer 114S2.

«Structure Example 5 of Unit 103S»

For example, the unit 103S includes the layer 114S, the layer 112, and the layer 113. A layer selected from functional layers such as a hole-transport layer, an electron-transport layer, and a carrier-blocking layer can be used for the unit 103S. A layer selected from functional layers such as a hole-injection layer, an electron-injection layer, an exciton-blocking layer, and a charge-generation layer can also be used for the unit 103S.

«Structure Example of Layer 114S»

The layer 114S is located between the layer 112 and the layer 113 and contains the electron-accepting material AM1 and the electron-donating material DM1.

«Structure Example of Layer 112»

The layer 112 is located between the electrode 551S and the layer 114S and contains a hole-transport material.

A hole-transport material can be used for the layer 112, for example. The layer 112 can be referred to as a hole-transport layer.

[Hole-Transport Material]

A material having a hole mobility of $1 \times 10^{-6}$ cm$^2$/Vs or higher can be suitably used as the hole-transport material.

As the hole-transport material, an amine compound or an organic compound having a π-electron rich heteroaromatic ring skeleton can be used, for example. Specifically, a compound having an aromatic amine skeleton, a compound having a carbazole skeleton, a compound having a thiophene skeleton, a compound having a furan skeleton, or the like can be used. The compound having an aromatic amine skeleton and the compound having a carbazole skeleton are particularly preferable because these compounds are highly reliable and have high hole-transport properties to contribute to a reduction in driving voltage.

The following are examples that can be used as a compound having an aromatic amine skeleton: 4,4'-bis[N-(1-naphthyl)-N-phenylamino]biphenyl (abbreviation: NPB), N,N'-bis(3-methylphenyl)-N,N'-diphenyl-[1,1'-biphenyl]-4, 4'-diamine (abbreviation: TPD), 4,4'-bis[N-(spiro-9,9'-bifluoren-2-yl)-N-phenyl amino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF).

As a compound having a carbazole skeleton, for example, 1,3-bis(N-carbazolyl)benzene (abbreviation: mCP), 4,4'-di (N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), or the like can be used.

As a compound having a thiophene skeleton, for example, 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), or the like can be used.

As a compound having a furan skeleton, for example, 4,4',4"-(benzene-1,3,5-triyl)tri(dibenzofuran) (abbreviation: DBF3P-II), 4-{3-[3-(9-phenyl-9H-fluoren-9-yl)phenyl]phenyl}dibenzofuran (abbreviation: mmDBFFLBi-II), or the like can be used. «Structure Example of Layer 113»

The layer 113 is located between the layer 114S and the electrode 552 and contains an electron-transport material.

An electron-transport material, a material having an anthracene skeleton, and a mixed material can be used for the layer 113, for example. The layer 113 can be referred to as an electron-transport layer.

[Electron-Transport Material]

For example, a metal complex or an organic compound having a π-electron deficient heteroaromatic ring skeleton can be used as the electron-transport material.

A material having an electron mobility higher than or equal to $1 \times 10^{-7}$ cm$^2$/Vs and lower than or equal to $5 \times 10^{-5}$ cm$^2$/Vs when the square root of the electric field strength [V/cm] is 600 can be suitably used as the electron-transport material.

For example, a material that can be used for the layer 104 can be used for the layer 113. Specifically, an electron-transport material that can be used as the composite material can be used for the layer 113.

[Material having Anthracene Skeleton]

An organic compound having an anthracene skeleton can be used for the layer 113. In particular, an organic compound having both an anthracene skeleton and a heterocyclic skeleton can preferably be used.

For example, an organic compound having both an anthracene skeleton and a nitrogen-containing five-membered ring skeleton can be used. Alternatively, an organic compound having both an anthracene skeleton and a nitrogen-containing five-membered ring skeleton where two heteroatoms are included in a ring can be used. Specifically, it is preferable to use, as the heterocyclic skeleton, a pyrazole ring, an imidazole ring, an oxazole ring, a thiazole ring, or the like.

For example, an organic compound having both an anthracene skeleton and a nitrogen-containing six-membered ring skeleton can be used. Alternatively, an organic compound having both an anthracene skeleton and a nitrogen-containing six-membered ring skeleton where two heteroatoms are included in a ring can be used. Specifically, it is preferable to use, as the heterocyclic skeleton, a pyrazine ring, a pyrimidine ring, a pyridazine ring, or the like.

[Structure Example of Mixed Material]

A material in which a plurality of kinds of substances are mixed can be used for the layer 113. Specifically, a mixed material which contains an alkali metal, an alkali metal compound, or an alkali metal complex and an electron-transport substance can be used for the layer 113.

This embodiment can be combined with any of the other embodiments in this specification as appropriate.

Embodiment 2

In this embodiment, a structure of an optical functional device of one embodiment of the present invention will be described with reference to FIGS. 2A to 2C and FIG. 3.

Figure 2A:
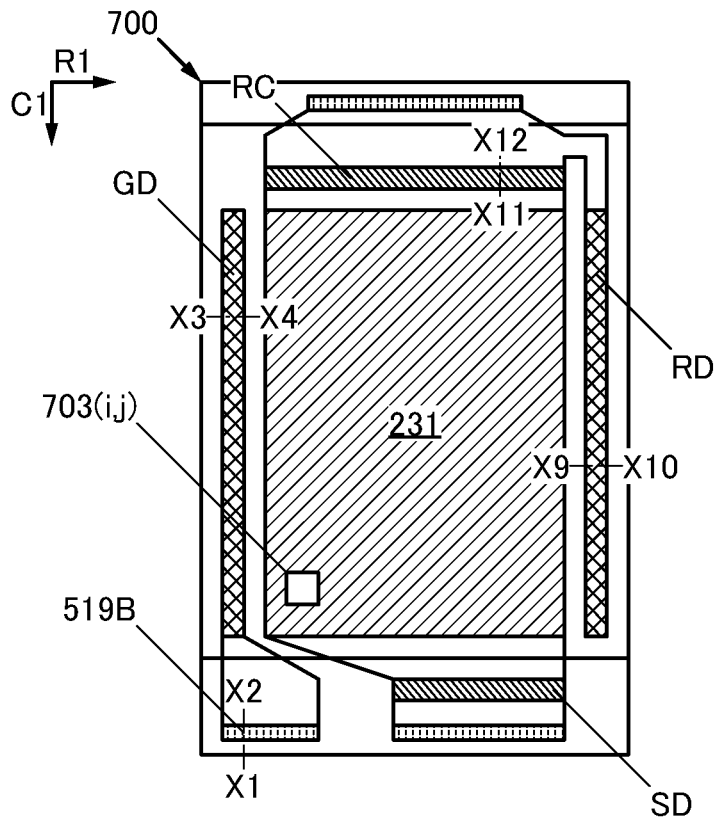
FIGS. 2A to 2C illustrate a structure of an optical functional device of an embodiment of the present invention.
Figure 2B:
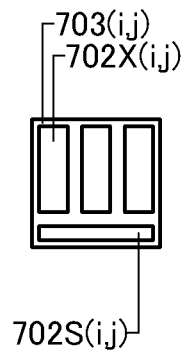
Figure 2C:
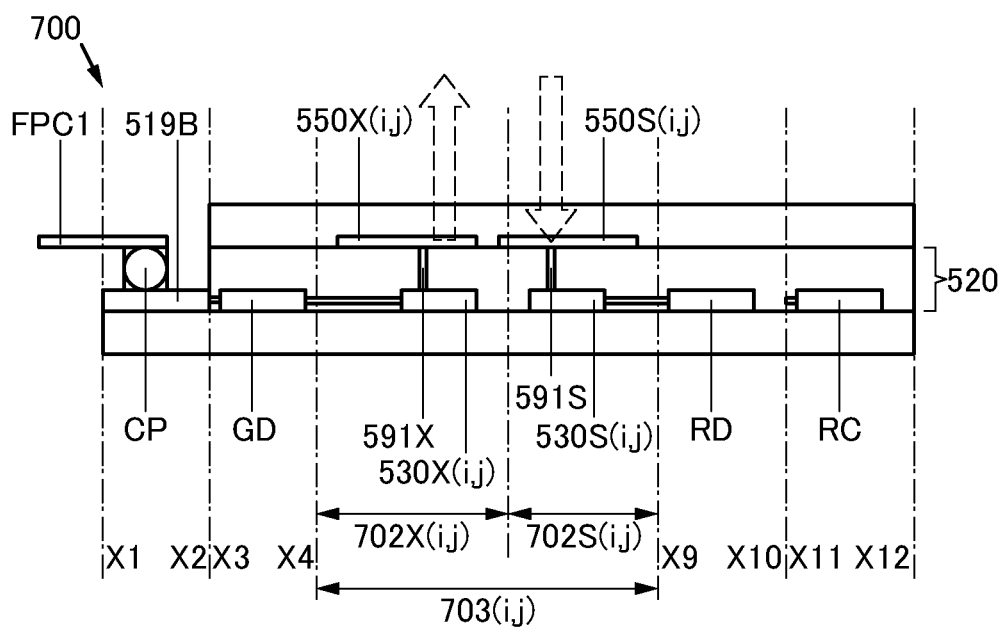

FIG. 2A is a top view of the optical functional device of one embodiment of the present invention, and FIG. 2B is a top view illustrating part of FIG. 2A. FIG. 2C is a cross-sectional view taken along lines X1-X2, X3-X4, X9-X10, and X11-X12 in FIG. 2A and in a pixel set 703(i,j).

Figure 3:
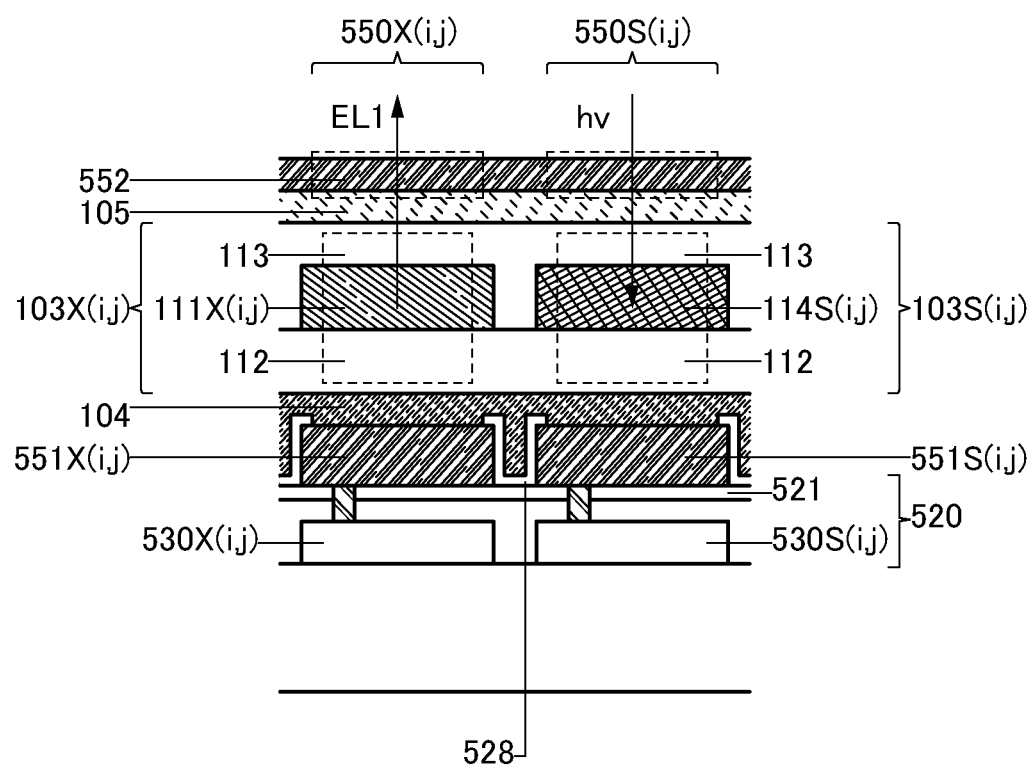
FIG. 3 illustrates a structure of an optical functional device of an embodiment of the present invention.

FIG. 3 is a cross-sectional view in a pixel set of the optical functional device of one embodiment of the present invention.

In this specification, an integer variable of 1 or more may be used for reference numerals. For example, "(p)" where p is an integer variable of 1 or more may be used for part of a reference numeral that specifies any one of up top components. For another example, "(m,n)" where each of m and n is an integer variable of 1 or more may be used for part of a reference numeral that specifies any one of up to m×n components.

In this specification and the like, a device formed using a metal mask or a fine metal mask (FMM) may be referred to as a device having a metal mask (MM) structure. In this specification and the like, a device formed without using a metal mask or an FMM may be referred to as a device having a metal maskless (MML) structure.

<Structure Example 1 of Optical Functional Device 700>

An optical functional device 700 described in this embodiment includes a region 231 (see FIG. 2A). The optical functional device 700 also includes a driver circuit GD, a driver circuit SD, a driver circuit RD, and a driver circuit RC.

The region 231 includes the pixel set 703(i,j), and the pixel set 703(i,j) includes a pixel 702X(i,j) and a pixel 702S(i,j) (see FIG. 2B).

The pixel 702X(i,j) includes a light-emitting device 550X(i,j) and the pixel circuit 530X(i,j). The light-emitting device 550X(i,j) is electrically connected to the pixel circuit 530X(i,j) through an opening 591X (see FIG. 2C).

The pixel 702S(i,j) includes a photoelectric conversion device 550S(i,j) and a pixel circuit 530S(i,j). The photoelectric conversion device 550S(i,j) is electrically connected to the pixel circuit 530S(i,j) through an opening 591S. The optical functional device 700 includes a functional layer 520 (see FIG. 2C). The functional layer 520 includes the pixel circuit 530X(i,j), the pixel circuit 530S(i,j), the driver circuit GD, the driver circuit SD, the driver circuit RD, and the driver circuit RC. The driver circuit GD supplies a control signal to the pixel circuit 530X(i,j), and the driver circuit SD supplies, for example, an image signal to the pixel circuit 530X(i,j). The driver circuit RD supplies a control signal to the pixel circuit 530S(i,j), and the driver circuit RC obtains, for example, an imaging signal from the pixel circuit 530S(i,j).

The optical functional device 700 includes a terminal portion 519B. The terminal portion 519B is electrically connected to flexible printed circuits FPC1 through a conductive material CP, for example.

<Structure Example 2 of Optical Functional Device 700>

The optical functional device 700 described in this embodiment includes the photoelectric conversion device 550S(i,j) and the light-emitting device 550X(i,j) adjacent to the photoelectric conversion device 550S(i,j) (see FIG. 2C).

For example, the photoelectric conversion device described in Embodiment 1 can be used as the photoelectric conversion device 550S(i,j).

For example, an organic EL device, a light-emitting diode, or the like can be used as the light-emitting device 550X(i,j).

Thus, the optical functional device 700 can not only display an image but also sense the distribution of ambient brightness, for example. In addition, the optical functional device 700 can not only display an image but also function as an optical touch sensor, for example. As a result, a novel optical functional device that is highly convenient, useful, or reliable can be provided.

<Structure Example of Photoelectric Conversion Device 550S(i,j)>

The photoelectric conversion device 550S(i,j) includes a unit 103S(i,j), an electrode 551S(i,j) and the electrode 552 (see FIG. 3). The unit 103S(i,j) is located between the electrode 551S(i,j) and the electrode 552. The electrode 551S(i,j) is formed over an insulating film 521, for example.

An insulating film 528 having an opening overlapping with the electrode 551S(i,j) is formed over the electrode 551S(i,j).

Specifically, a structure that can be used for the unit 103S described in Embodiment 1 can be used for the unit 103S (i,j), and a structure that can be used for the electrode 551S described in Embodiment 1 can be used for the electrode 551S(i,j). A structure that can be used for the layer 114S described in Embodiment 1 can be used for the layer 114S(i,j).

<Structure Example of Light-Emitting Device 550X(i,j)>

For example, the light-emitting device 550X(i,j) includes the unit 103X(i,j), an electrode 551X(if), and the electrode 552 (see FIG. 3). The unit 103X(i,j) is located between the electrode 551X(i,j) and the electrode 552. The electrode 551X(i,j) is formed over the insulating film 521, for example. The insulating film 528 having an opening overlapping with the electrode 551X(i,j) is formed over the electrode 551X(i,j). <Structure example of unit 103X(i,j)>

The unit 103X(i,j) has a single-layer structure or a stacked-layer structure. For example, the unit 103X(i,j) includes a layer 111X(i,j), the layer 112, and the layer 113. The unit 103 has a function of emitting light EL1.

The layer 112 is located between the electrode 551X(i,j) and the layer 111X(i,j), and the layer 113 is located between the layer 111X(i,j) and the electrode 552.

For example, a layer selected from functional layers such as a light-emitting layer, a hole-transport layer, an electron-transport layer, and a carrier-blocking layer can be used for the unit 103X(i,j). A layer selected from functional layers such as a hole-injection layer, an electron-injection layer, an exciton-blocking layer, and a charge-generation layer can also be used for the unit 103X(i,j).

«Structure Example of Layer 112»

A hole-transport material can be used for the layer 112, for example. The layer 112 can be referred to as a hole-transport layer. A material having a wider bandgap than the light-emitting material contained in the layer 111X(i,j) is preferably used for the layer 112. In that case, transfer of energy from excitons generated in the layer 111X(i,j) to the layer 112 can be inhibited.

[Hole-Transport Material]

A material having a hole mobility of $1 \times 10^{-6}$ cm$^2$/Vs or higher can be suitably used as the hole-transport material.

For example, a hole-transport material that can be used for the layer 112 described in Embodiment 1 can be used for the layer 112.

«Structure Example of Layer 113»

An electron-transport material, a material having an anthracene skeleton, and a mixed material can be used for the layer 113, for example. The layer 113 can be referred to as an electron-transport layer. A material having a wider bandgap than the light-emitting material contained in the layer 111X(i,j) is preferably used for the layer 113. In that case, energy transfer from excitons generated in the layer 111X(i,j) to the layer 113 can be inhibited.

[Electron-Transport Material]

For example, a metal complex or an organic compound having a π-electron deficient heteroaromatic ring skeleton can be used as the electron-transport material.

For example, an electron-transport material that can be used for the layer 113 described in Embodiment 1 can be used for the layer 113.

«Structure Example 1 of Layer 111X(i,j)»

The layer 111X(i,j) contains a light-emitting material. Alternatively, a light-emitting material and a host material can be used for the layer 111X(i,j). The layer 111X(i,j) can be referred to as a light-emitting layer. The layer 111X(i,j) is preferably provided in a region where holes and electrons are recombined. This allows efficient conversion of energy generated by recombination of carriers into light and emission of the light.

Furthermore, the layer 111X(i,j) is preferably provided apart from a metal used for the electrode or the like. In that case, a quenching phenomenon caused by the metal used for the electrode or the like can be inhibited.

It is preferable that a distance from an electrode or the like having reflectivity to the layer 111X(i,j) be adjusted and the layer 111X(i,j) be placed in an appropriate position in accordance with an emission wavelength. With this structure, the amplitude can be increased by utilizing an interference phenomenon between light reflected by the electrode or the like and light emitted from the layer 111X(i,j). Light with a predetermined wavelength can be intensified and the spectrum of the light can be narrowed. In addition, bright light emission colors with high intensity can be obtained. In other words, the layer 111X(i,j) is placed in an appropriate position, for example, between electrodes and the like, and thus a microcavity structure can be formed.

For example, a fluorescent substance, a phosphorescent substance, or a substance exhibiting thermally activated delayed fluorescence (TADF) (also referred to as a TADF material) can be used for the light-emitting material. Thus, energy generated by recombination of carriers can be released as light EL1 from the light-emitting material (see FIG. 3).

Thus, part of a manufacturing process for the light-emitting device can be utilized as part of a manufacturing process for the photoelectric conversion device. Furthermore, a new value can be added with use of an existing manufacturing line of light-emitting devices. As a result, a novel optical functional device that is highly convenient, useful, or reliable can be provided.

[Fluorescent Substance]

A fluorescent substance can be used for the layer 111X (i,j). For example, the following fluorescent substances can be used for the layer 111X(i,j). Note that fluorescent substances that can be used for the layer 111X(i,j) are not limited to the following, and a variety of known fluorescent substances can be used.

Specifically, any of the following fluorescent substances can be used: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N,N'-(pyrene-1,6-diyl)bis[(6,N-diphenylbenzo[b]naphtho[1,2-d]furan)-8-amine] (abbreviation: 1,6BnfAPm-03), 3,10-bis[N-(9-phenyl-9H-carbazol-2-yl)-N-phenylamino]naphtho[2,3-b;6, 7-V]bisbenzofuran (abbreviation: 3,10PCA2Nbf(IV)-02), 3,10-bis[N-(dibenzofuran-3-yl)-N-phenylamino]naphtho[2,3-b;6,7-b']bisbenzofuran (abbreviation: 3,10FrA2Nbf(IV)-02), and the like.

Condensed aromatic diamine compounds typified by pyrenediamine compounds such as 1,6FLPAPrn, 1,6mMemFLPAPrn, and 1,6BnfAPm-03 are particularly preferable because of their high hole-trapping properties, high emission efficiency, or high reliability.

Other examples of fluorescent substances include N-[4-(9,10-diphenyl-2-anthryl)phenyl]-N,N',N'-triphenyl-1,4-phenylenediamine (abbreviation: 2DPAPPA), N,N,N',N',N'',N''',N''''-octaphenyldibenzo[g,p]chrysene-2,7,10,15-tetraamine (abbreviation: DBC1), coumarin 30, 9,10-diphenyl-2-[N-phenyl-N-(9-phenyl-carbazol-3-yl)-amino]-anthracene (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N''-triphenyl-1,4-phenylenediamine (abbreviation: 2DPAPA), N-[9,10-bis(1,1'-biphenyl-2-yl)-2-anthryl]-N,N',N''-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracene-2-amine (abbreviation: 2YGABPhA), N,N,9-triphenylanthracene-9-amine (abbreviation: DPhAPhA), coumarin 545T, N,N'-diphenylquinacridone (abbreviation: DPQd), rubrene, and 5,12-bis(1,1'-biphenyl-4-yl)-6,11-diphenyltetracene (abbreviation: BPT).

Other examples of fluorescent substances include 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

[Phosphorescent Substance]

A phosphorescent substance can be used for the layer 111X(i,j). For example, phosphorescent substances described below as examples can be used for the layer 111X(i,j). Note that phosphorescent substances that can be used for the layer 111X(i,j) are not limited to the following, and a variety of known phosphorescent substances can be used for the layer 111X(i,j).

For example, any of the following can be used for the layer 111X(i,j): an organometallic iridium complex having a 4H-triazole skeleton, an organometallic iridium complex having a 1H-triazole skeleton, an organometallic iridium complex having an imidazole skeleton, an organometallic iridium complex having a phenylpyridine derivative with an electron-withdrawing group as a ligand, an organometallic iridium complex having a pyrimidine skeleton, an organometallic iridium complex having a pyrazine skeleton, an organometallic iridium complex having a pyridine skeleton, a rare earth metal complex, a platinum complex, and the like.

[Phosphorescent Substance (Blue)]

As an organometallic iridium complex having a 4H-triazole skeleton or the like, tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris [4-(3-biphenyl)-5-isopropyl-3-phenyl-4H-1,2,4-triazolato]iridium(III) (abbreviation: [Ir(iPrptz-3b)$_3$]), or the like can be used.

As an organometallic iridium complex having a 1H-triazole skeleton or the like, tris [3-methyl-1-(2-methylphenyl)-5-phenyl-1H-1,2,4-triazolato]iridium(III) (abbreviation: [Ir(Mptz1-mp)$_3$]), tris(1-methyl-5-phenyl-3-propyl-1H-1,2,4-triazolato)iridium(III) (abbreviation: [Ir(Prptz1-Me)$_3$]), or the like can be used.

As an organometallic iridium complex having an imidazole skeleton or the like, fac-tris[1-(2,6-diisopropylphenyl)-2-phenyl-1H-imidazole]iridium(III) (abbreviation: [Ir(iPrpmi)$_3$]), tris[3-(2,6-dimethylphenyl)-7-methylimidazo[1,2-f]phenanthridinato]iridium(III) (abbreviation: [Ir(dmpimpt-Me)$_3$]), or the like can be used.

As an organometallic iridium complex having a phenylpyridine derivative with an electron-withdrawing group as a ligand, or the like, bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$] iridium(III) picolinate (abbreviation: FIrpic), bis{2-[4',5'-bis(trifluoromethyl)phenyl]pyridinato-N,C$^{2'}$}iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), or the like can be used.

These substances are compounds exhibiting blue phosphorescent light and having an emission wavelength peak at 440 nm to 520 nm.

[Phosphorescent Substance (Green)]

As an organometallic iridium complex having a pyrimidine skeleton or the like, tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis(4,6-diphenylpyrimidinato)iridium(III) (abbreviation: [Ir(dppm)$_2$(acac)]), or the like can be used.

As an organometallic iridium complex having a pyrazine skeleton or the like, (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), or the like can be used.

As an organometallic iridium complex having a pyridine skeleton or the like, tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation:

[Ir(pq)₃]), bis(2-phenylquinolinato-N,C²')iridium(III) acetylacetonate (abbreviation: [Ir(pq)₂(acac)]), [2-d3-methyl-8-(2-pyridinyl-κN)benzofuro[2,3-b]pyridine-κC]bis[2-(5-d3-methyl-2-pyridinyl-κN2)phenyl-κC]iridium(III) (abbreviation: [Ir(5mppy-d3)₂(mbfpypy-d3)]), [2-d3-methyl-(2-pyridinyl-κN)benzofuro[2,3-b]pyridine-κC]bis[2-(2-pyridinyl-κN)phenyl-κC]iridium(III) (abbreviation: [Ir(ppy)₂(mbfpypy-d3)]), or the like can be used.

Examples of a rare earth metal complex are tris(acetylacetonato) (monophenanthroline)terbium(III) (abbreviation: Tb(acac)₃(Phen)), and the like.

These are compounds that mainly exhibit green phosphorescent light and have an emission wavelength peak at 500 nm to 600 nm. Note that an organometallic iridium complex having a pyrimidine skeleton has distinctively high reliability or emission efficiency.

[Phosphorescent Substance (Red)]

As an organometallic iridium complex having a pyrimidine skeleton or the like, (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), bis[4,6-di(naphthalen-1-yl)pyrimidinato](dipivaloylmethanato)iridium(III) (abbreviation: [Ir(d1pm)₂(dpm)]), or the like can be used.

As an organometallic iridium complex having a pyrazine skeleton or the like, (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), (acetylacetonato)bis[2,3-bis(4-fluorophenyl)quinoxalinato]iridium(III) (abbreviation: [Ir(Fdpq)₂(acac)]), or the like can be used.

As an organometallic iridium complex having a pyridine skeleton or the like, tris(1-phenylisoquinolinato-N,C²') iridium(III) (abbreviation: [Ir(piq)₃]), bis(1-phenylisoquinolinato-N,C²')iridium(III) acetylacetonate (abbreviation: [Ir(piq)₂(acac)]), or the like can be used.

As a rare earth metal complex or the like, tris(1,3-diphenyl-1,3-propanedionato)(monophenanthroline)europium(III) (abbreviation: [Eu(DBM)₃(Phen)]), tris[1-(2-thenoyl)-3,3,3-trifluoroacetonato](monophenanthroline)europium(III) (abbreviation: [Eu(TTA)₃(Phen)]), or the like can be used.

As a platinum complex or the like, 2,3,7,8,12,13,17,18-octaethyl-21H,23H-porphyrin platinum(II) (abbreviation: PtOEP) or the like can be used.

These compounds emit red phosphorescent light having an emission peak at 600 nm to 700 nm. Furthermore, the organometallic iridium complexes having a pyrazine skeleton can provide red light emission with chromaticity favorably used for display devices.

[Substance Exhibiting Thermally Activated Delayed Fluorescence (TADF)]

A TADF material can be used for the layer 111X(i,j). For example, any of the TADF materials enumerated below can be used as the light-emitting material. Note that TADF materials that can be used as the light-emitting material are not limited to the following, and a variety of known TADF materials can be used as the light-emitting material.

In the TADF material, the difference between the S1 level and the T1 level is small, and reverse intersystem crossing (upconversion) from the triplet excited state into the singlet excited state can be achieved by a small amount of thermal energy. Thus, the singlet excited state can be efficiently generated from the triplet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy. A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

Examples of the TADF material include a fullerene, a derivative thereof, an acridine, a derivative thereof, and an eosin derivative. Furthermore, porphyrin containing a metal such as magnesium (Mg), zinc (Zn), cadmium (Cd), tin (Sn), platinum (Pt), indium (In), or palladium (Pd) can be also used for the TADF material.

Specifically, the following materials whose structural formulae are shown below can be used: a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), an octaethylporphyrin-platinum chloride complex (PtCl₂OEP), and the like.

[Chemical Formulae 5]

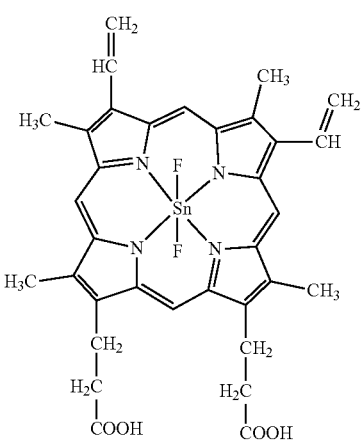

SnF₂(Proto IX)

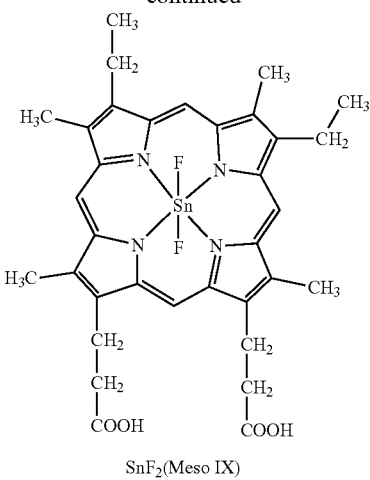

SnF₂(Meso IX)

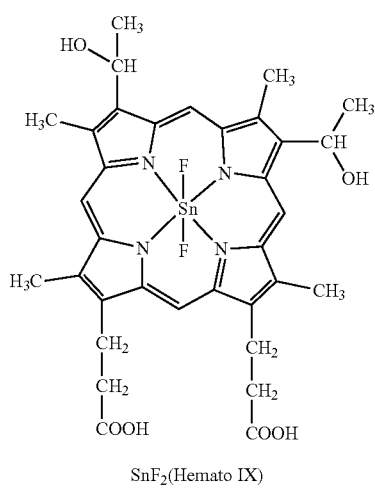

SnF₂(Hemato IX)

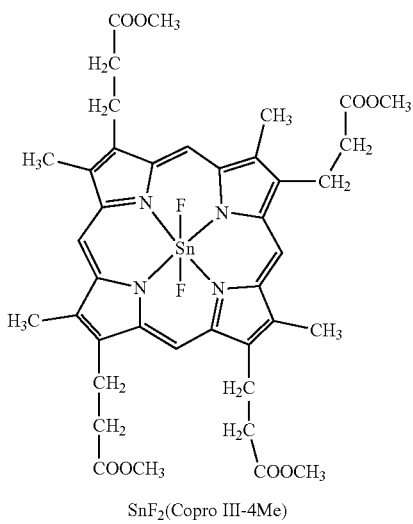

SnF₂(Copro III-4Me)

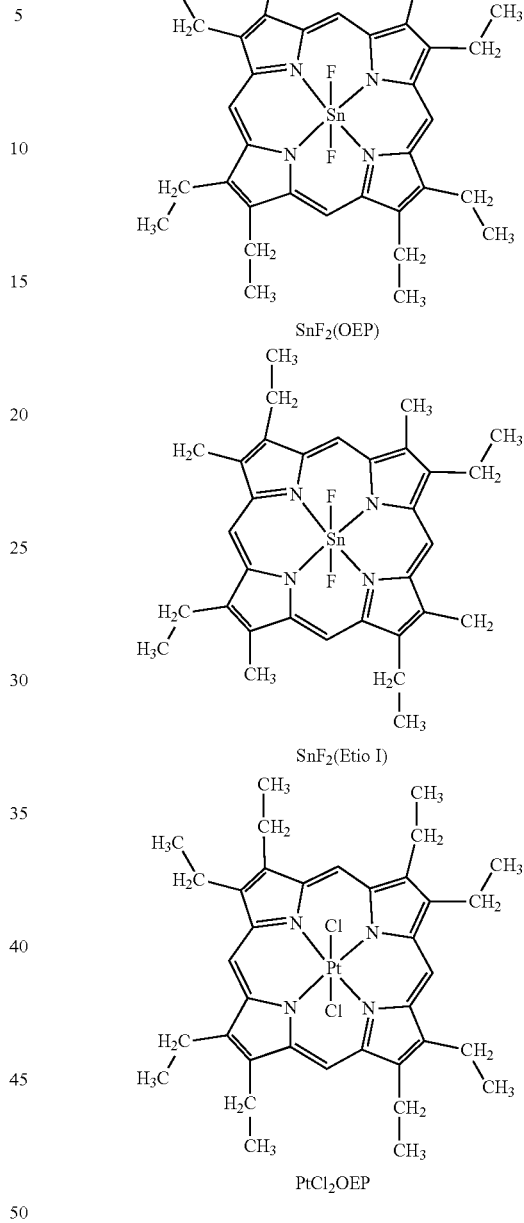

SnF₂(OEP)

SnF₂(Etio I)

PtCl₂OEP

Furthermore, a heterocyclic compound including one or both of a π-electron rich heteroaromatic ring and a π-electron deficient heteroaromatic ring can be used, for example, as the TADF material.

Specifically, the following compounds whose structural formulae are shown below can be used: 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), and the like.
[Chemical Formulae 6]
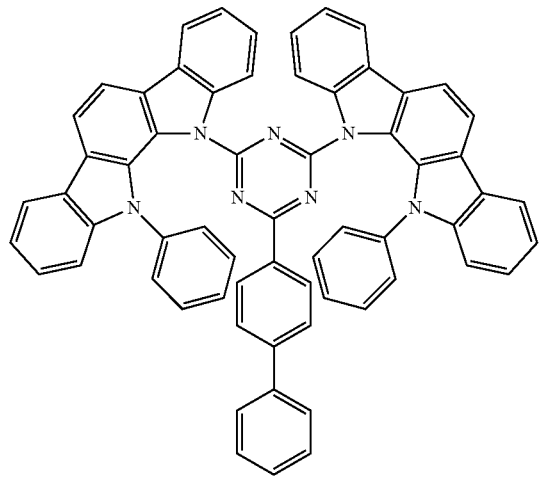
PIC-TRZ
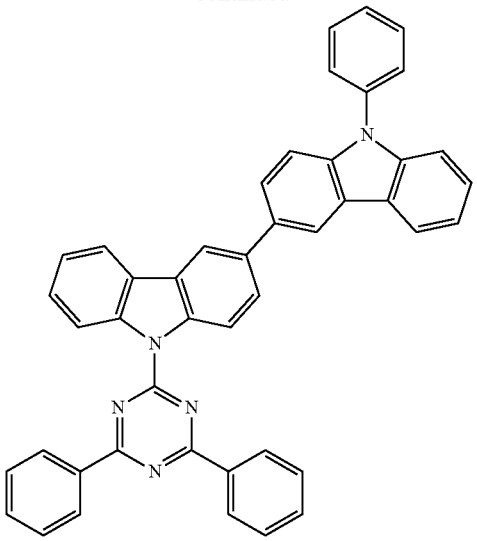
PCCzTzn
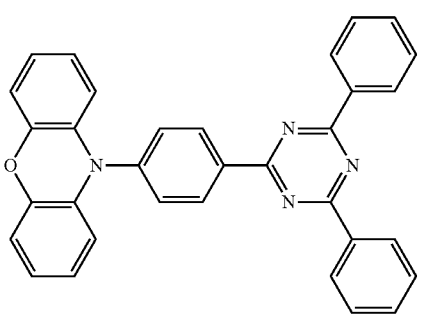
PXZ-TRZ
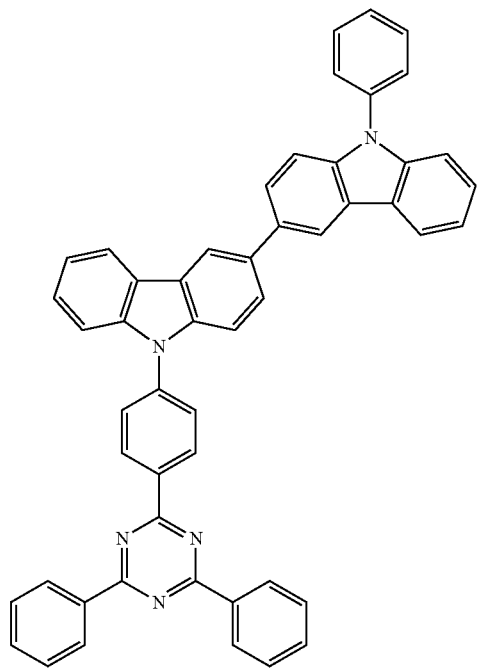
PCCzPTzn
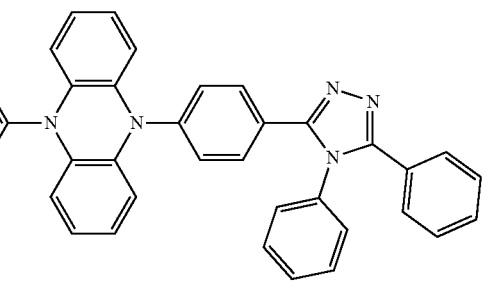
PPZ-3TPT
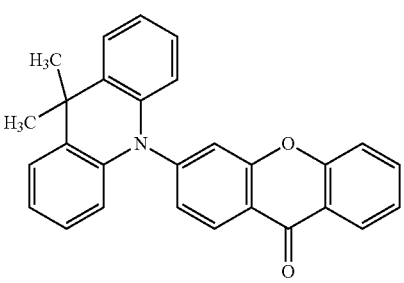
ACRXTN

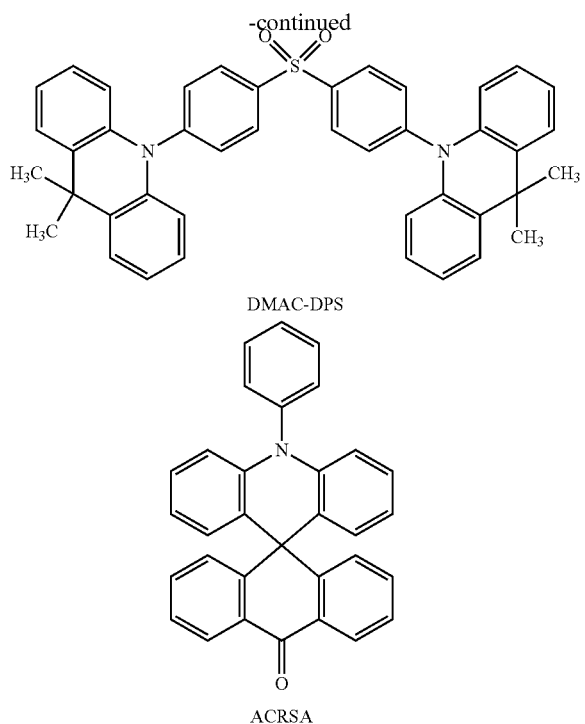

DMAC-DPS

ACRSA

Such a heterocyclic compound is preferable because of having high electron-transport and hole-transport properties owing to a π-electron rich heteroaromatic ring and a π-electron deficient heteroaromatic ring. Among skeletons having the π-electron deficient heteroaromatic ring, in particular, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high electron-accepting properties and high reliability.

Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable.

Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used.

As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane and boranthrene, an aromatic ring or a heteroaromatic ring having a nitrile group or a cyano group such as benzonitrile or cyanobenzene, a carbonyl skeleton such as benzophenone, a phosphine oxide skeleton, a sulfone skeleton, or the like can be used.

As described above, a π-electron deficient skeleton and a π-electron rich skeleton can be used instead of at least one of the π-electron deficient heteroaromatic ring and the π-electron rich heteroaromatic ring.

«Structure Example 2 of Layer 111X(i,j)»

A carrier-transport material can be used as the host material. For example, a hole-transport material, an electron-transport material, a TADF material, a material having an anthracene skeleton, or a mixed material can be used as the host material. A material having a wider bandgap than the light-emitting material contained in the layer 111X(i,j) is preferably used as the host material. Thus, transfer of energy from excitons generated in the layer 111X(i,j) to the host material can be inhibited.

[Hole-Transport Material]

A material having a hole mobility of $1 \times 10^{-6}$ cm$^2$/Vs or higher can be suitably used as the hole-transport material.

For example, a hole-transport material that can be used for the layer 112 can be used for the layer 111X(i,j). Specifically, a hole-transport material that can be used for the hole-transport layer can be used for the layer 111X(i,j).

[Electron-Transport Material]

For example, a metal complex or an organic compound having a π-electron deficient heteroaromatic ring skeleton can be used as the electron-transport material.

For example, an electron-transport material that can be used for the layer 113 can be used for the layer 111X(i,j). Specifically, an electron-transport material that can be used for the electron-transport layer can be used for the layer 111X(i,j).

[Material having Anthracene Skeleton]

An organic compound having an anthracene skeleton can be used as the host material. An organic compound having an anthracene skeleton is particularly preferable in the case where a fluorescent substance is used as a light-emitting substance. Thus, a light-emitting device with high emission efficiency and high durability can be obtained.

Among the organic compounds having an anthracene skeleton, an organic compound having a diphenylanthracene skeleton, in particular, a 9,10-diphenylanthracene skeleton, is chemically stable and thus is preferable. The host material preferably has a carbazole skeleton because the hole-injection and hole-transport properties are improved. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Note that in terms of the hole-injection and hole-transport properties, instead of a carbazole skeleton, a benzofluorene skeleton or a dibenzofluorene skeleton may be used.

Thus, a substance having both a 9,10-diphenylanthracene skeleton and a carbazole skeleton, a substance having both a 9,10-diphenylanthracene skeleton and a benzocarbazole skeleton, or a substance having both a 9,10-diphenylanthracene skeleton and a dibenzocarbazole skeleton is preferable as the host material.

Examples of the substances that can be used include 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 9-(1-naphthyl)-10-[4-(2-naphthyl)phenyl]anthracene (abbreviation: αN-βNPAnth), 9-phenyl-3-[4-(10-phenyl-9-anthryl)phenyl]-9H-carbazole (abbreviation: PCzPA), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 3-[4-(1-naphthyl)-phenyl]-9-phenyl-9H-carbazole (abbreviation: PCPN), and the like.

In particular, CzPA, cgDBCzPA, 2mBnfPPA, and PCzPA have excellent characteristics.

[Substance Exhibiting Thermally Activated Delayed Fluorescence (TADF)]

A TADF material can be used as the host material. When the TADF material is used as the host material, triplet excitation energy generated in the TADF material can be converted into singlet excitation energy by reverse intersystem crossing. Moreover, excitation energy can be transferred to the light-emitting substance. In other words, the TADF material functions as an energy donor, and the light-emitting substance functions as an energy acceptor. Thus, the emission efficiency of the light-emitting device can be increased.

This is very effective in the case where the light-emitting substance is a fluorescent substance. In that case, the S1 level of the TADF material is preferably higher than that of the fluorescent substance in order that high emission efficiency be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protecting group around a luminophore (a skeleton which causes light emission) of the fluorescent substance. As the protecting group, a substituent having no π bond and a saturated hydrocarbon are preferably used. Specific examples include an alkyl group having 3 to 10, inclusive, carbon atoms, a cycloalkyl group having 3 to 10, inclusive, carbon atoms, and a trialkylsilyl group having 3 to 10, inclusive, carbon atoms. It is further preferable that the fluorescent substance have a plurality of protecting groups. The substituents having no π bond are poor in carrier-transport performance; therefore, the TADF material and the luminophore of the fluorescent substance can be made away from each other with little influence on carrier-transportation or carrier recombination.

Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring.

Examples of the condensed aromatic ring or the condensed heteroaromatic ring include a phenanthrene skeleton, a stilbene skeleton, an acridone skeleton, a phenoxazine skeleton, and a phenothiazine skeleton. In particular, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield. For example, the TADF material that can be used as the light-emitting material can be used as the host material.

[Structure Example 1 of Mixed Material]

A material in which a plurality of kinds of substances are mixed can be used as the host material. For example, a material which includes an electron-transport material and a hole-transport material can be used as the mixed material. The weight ratio between the hole-transport material and the electron-transport material contained in the mixed material may be (the hole-transport material/the electron-transport material)=(1/19) or more and (19/1) or less. Thus, the carrier-transport property of the layer $111X(i,j)$ can be easily adjusted and a recombination region can be easily controlled.

[Structure Example 2 of Mixed Material]

In addition, a material mixed with a phosphorescent substance can be used as the host material. When a fluorescent substance is used as the light-emitting substance, a phosphorescent substance can be used as an energy donor for supplying excitation energy to the fluorescent substance.

[Structure Example 3 of Mixed Material]

A mixed material containing a material to form an exciplex can be used as the host material. For example, a material in which an emission spectrum of a formed exciplex overlaps with a wavelength of the absorption band on the lowest energy side of the light-emitting substance can be used as the host material. This enables smooth energy transfer and improves emission efficiency. An increase in the driving voltage can be inhibited. With such a structure, light emission can be efficiently obtained by exciplex—triplet energy transfer (ExTET), which is energy transfer from the exciplex to the light-emitting substance (phosphorescent material).

A phosphorescent substance can be used as at least one of the materials forming an exciplex. Accordingly, reverse intersystem crossing can be used. Triplet excitation energy can be efficiently converted into singlet excitation energy.

Combination of an electron-transport material and a hole-transport material whose HOMO level is higher than or equal to that of the electron-transport material is preferable for forming an exciplex. The LUMO level of the hole-transport material is preferably higher than or equal to the LUMO level of the electron-transport material. Thus, an exciplex can be efficiently formed. Note that the LUMO levels and the HOMO levels of the materials can be derived from the electrochemical characteristics (the reduction potentials and the oxidation potentials). Specifically, the reduction potentials and the oxidation potentials can be measured by cyclic voltammetry (CV).

The formation of an exciplex can be confirmed by a phenomenon in which the emission spectrum of the mixed film in which the hole-transport material and the electron-transport material are mixed is shifted to the longer wavelength side than the emission spectra of each of the materials (or has another peak on the longer wavelength side) observed by comparison of the emission spectra of the hole-transport material, the electron-transport material, and the mixed film of these materials, for example. Alternatively, the formation of an exciplex can be confirmed by a difference in transient response, such as a phenomenon in which the transient PL lifetime of the mixed film has longer lifetime components or a larger proportion of delayed components than that of each of the materials, observed by comparison of transient photoluminescence (PL) of the hole-transport material, the electron-transport material, and the mixed film of the materials. The transient PL can be rephrased as transient electroluminescence (EL). That is, the formation of an exciplex can also be confirmed by a difference in transient response observed by comparison of the transient EL of the hole-transport material, the electron-transport material, and the mixed film of the materials.

Note that this embodiment can be combined with any of the other embodiments in this specification as appropriate.

Embodiment 3

Figure 4:
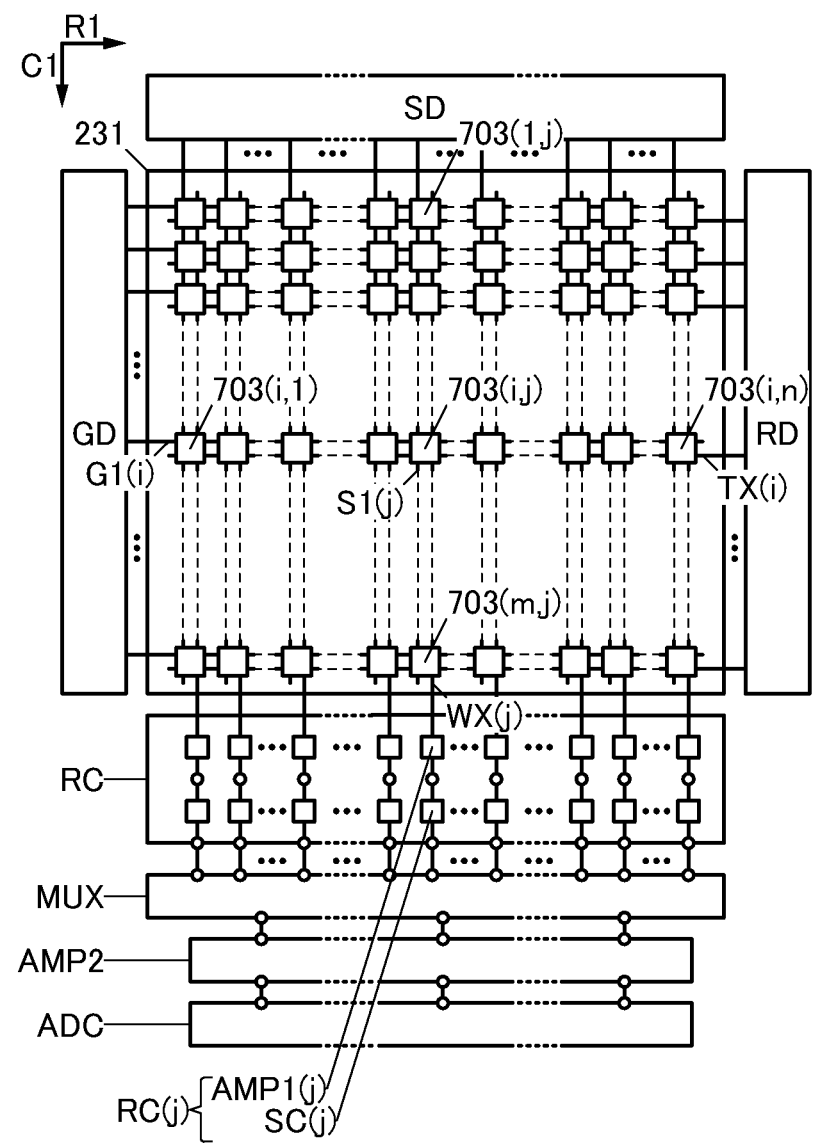
FIG. 4 illustrates a structure of an optical functional device of an embodiment of the present invention.

In this embodiment, the structure of a device of one embodiment of the present invention will be described with reference to FIGS. 2A to 2C and FIG. 4 to FIG. 7B. FIG. 4 is a block diagram illustrating the configuration of a device of one embodiment of the present invention.

Figure 5:
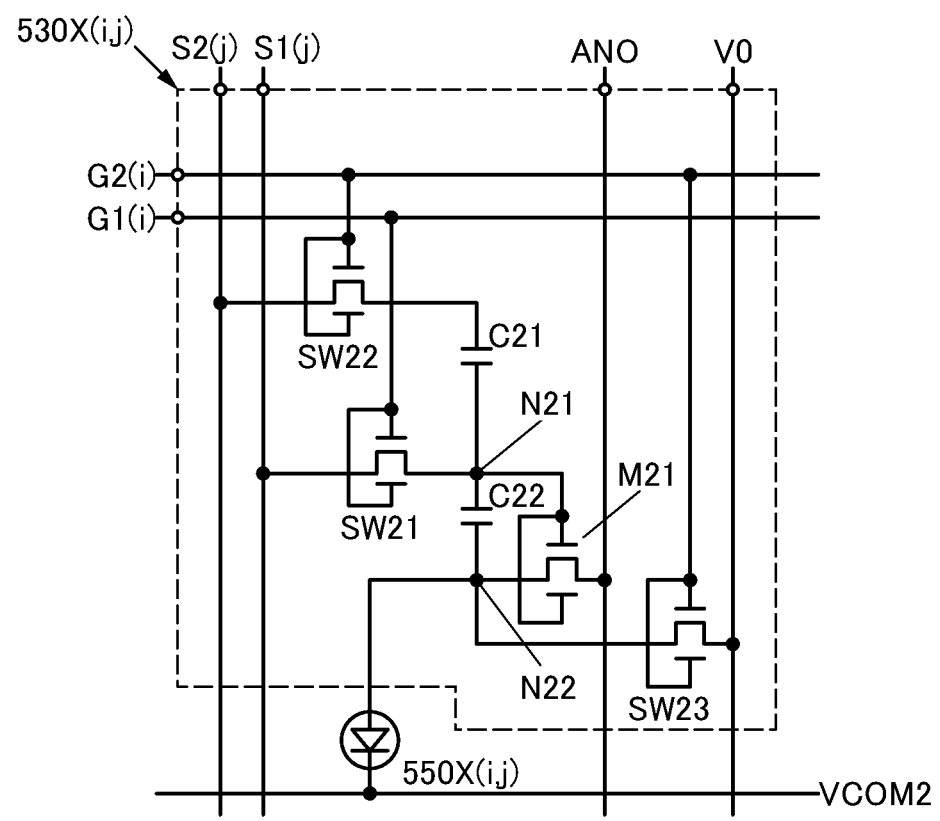
FIG. 5 is a circuit diagram illustrating a configuration of an optical functional device of an embodiment of the present invention.

FIG. 5 is a circuit diagram illustrating the configuration of a device of one embodiment of the present invention.

Figure 6:
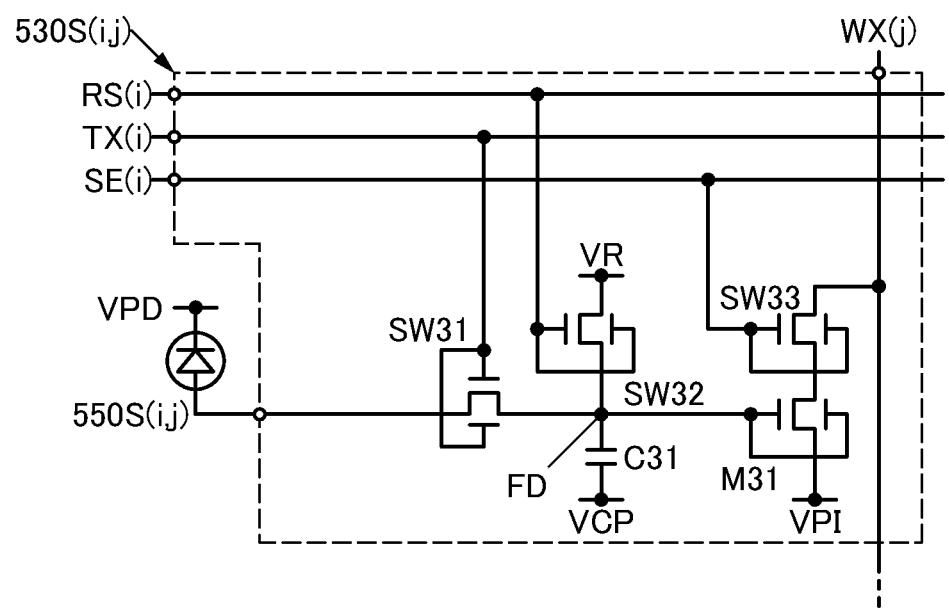
FIG. 6 is a circuit diagram illustrating a configuration of an optical functional device of an embodiment of the present invention.

FIG. 6 is a circuit diagram illustrating the configuration of a device of one embodiment of the present invention.

Figure 7A:
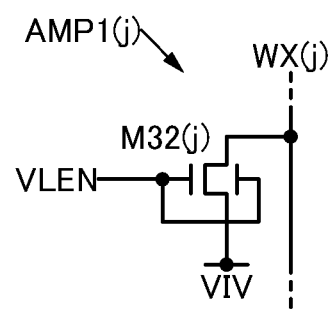
FIGS. 7A and 7B are circuit diagrams illustrating an optical functional device of an embodiment of the present invention.
Figure 7B:
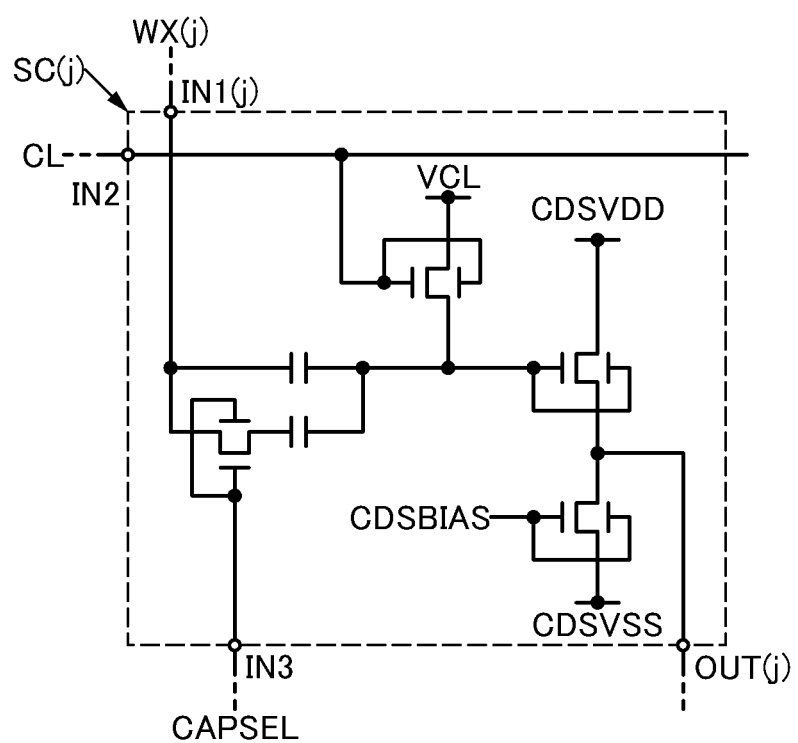

FIGS. 7A and 7B are circuit diagrams each illustrating the configuration of a device of one embodiment of the present invention. FIG. 7A is a circuit diagram illustrating an amplifier circuit AMP1 that can be used in a device of one embodiment of the present invention. FIG. 7B is a circuit diagram of a sampling circuit SC(j) that can be used in a device or an optical functional device of one embodiment of the present invention.

<Structure Example 1 of Optical Functional Device 700>

The optical functional device 700 of one embodiment of the present invention includes the pixel set 703($i,j$), a conductive film ANO, and a conductive film VCOM2 (see FIG. 2C and FIG. 5). The optical functional device 700 has a function of displaying an image.

«Structure Example 1 of Pixel Set 703($i,j$)»

The pixel set 703($i,j$) includes the pixel 702X(i,j) (see FIGS. 2B and 2C).

The pixel 702X(i,j) includes a light-emitting device 550X(i,j) and the pixel circuit 530X(i,j). The light-emitting device 550X(i,j) includes a pair of electrodes; one of the electrodes is electrically connected to the pixel circuit 530X(i,j) and the other electrode is electrically connected to the conductive film VCOM2.

For example, the light-emitting device described in Embodiment 2 can be used as the light-emitting device 550X(i,j).

The pixel circuit 530X(i,j) is electrically connected to the conductive film ANO (see FIG. 5).

<Structure Example 2 of Optical Functional Device 700>

The optical functional device 700 of one embodiment of the present invention includes the pixel set 703($i,j$), a conductive film WX(j), and a conductive film VPD (see FIG. 2C and FIG. 6). The optical functional device 700 has a function of supplying an imaging signal.

«Structure Example 2 of Pixel Set 703($i,j$)»

The pixel set 703($i,j$) includes the pixel 702S(i,j) (see FIGS. 2B and 2C).

The pixel 702S(i,j) includes the photoelectric conversion device 550S(i,j) and the pixel circuit 530S(i,j). The photoelectric conversion device 550S(i,j) includes a pair of electrodes; one of the electrodes is electrically connected to the pixel circuit 530S(i,j) and the other electrode is electrically connected to the conductive film VPD.

For example, the photoelectric conversion device described in Embodiment 1 can be used as the photoelectric conversion device 550S(i,j).

The pixel circuit 530S(i,j) is electrically connected to a conductive film WX(i) and has a function of supplying an imaging signal (see FIG. 6).

<Structure Example 3 of Optical Functional Device 700>

The optical functional device 700 of one embodiment of the present invention includes the driver circuit GD, a conductive film G1($i$), and a conductive film G2($i$) (see FIG. 4 and FIG. 5).

«Configuration Example of Driver Circuit GD»

The driver circuit GD supplies a first selection signal and a second selection signal.

The conductive film G1($i$) is supplied with the first selection signal, and the conductive film G2($i$) is supplied with the second selection signal.

<Structure Example 4 of Optical Functional Device 700>

The optical functional device 700 of one embodiment of the present invention includes the driver circuit SD, the conductive film S1($j$), and the conductive film S2($j$) (see FIG. 4 and FIG. 5). The optical functional device 700 also includes a conductive film V0.

«Configuration Example of Driver Circuit SD»

The driver circuit SD supplies a first control signal and a second control signal.

The conductive film S1($j$) is supplied with the first control signal, and the conductive film S2($j$) is supplied with the second control signal.

«Configuration Example 1 of Pixel Circuit 530X(i,j)»

The pixel circuit 530X(i,j) is electrically connected to the conductive film G1($i$) and the conductive film S1($j$). The conductive film G1($i$) supplies the first selection signal, and the conductive film S1($j$) supplies the first control signal.

The pixel circuit 530X(i,j) drives the light-emitting device 550X(i,j) in response to the first selection signal and the first control signal. The light-emitting device 550X(i,j) emits light.

«Configuration Example 2 of Pixel Circuit 530X(i,j)»

The pixel circuit 530X(i,j) includes a switch SW21, a switch SW22, a transistor M21, a capacitor C21, and a node N21.

The transistor M21 includes a gate electrode electrically connected to the node N21, a first electrode electrically connected to the light-emitting device 550X(i,j), and a second electrode electrically connected to the conductive film ANO.

The switch SW21 includes a first terminal electrically connected to the node N21, a second terminal electrically connected to the conductive film S1($j$), and a gate electrode having a function of controlling an on/off state of the switch SW21 according to the potential of the conductive film G1($i$).

The switch SW22 includes a first terminal electrically connected to the conductive film S2($j$), and a gate electrode having a function of controlling an on/off state of the switch SW22 according to the potential of the conductive film G2($i$).

The capacitor C21 includes a conductive film electrically connected to the node N21 and a conductive film electrically connected to a second electrode of the switch SW22.

Accordingly, an image signal can be stored in the node N21. Alternatively, the potential of the node N21 can be changed using the switch SW22. Alternatively, the intensity of light emitted from the light-emitting device 550X(i,j) can be controlled with the potential of the node N21. As a result, a novel device that is highly convenient, useful, or reliable can be provided.

«Configuration Example 3 of Pixel Circuit 530X(i,j)»

The pixel circuit 530X(i,j) includes a switch SW23, a node N22, and a capacitor C22.

The switch SW23 includes a first terminal electrically connected to the conductive film VO, a second terminal electrically connected to the node N22, and a gate electrode having a function of controlling an on/off state of the switch SW23 according to the potential of the conductive film G2(i).

The capacitor C22 includes a conductive film electrically connected to the node N21 and a conductive film electrically connected to the node N22.

The first electrode of the transistor M21 is electrically connected to the node N22.

<Structure Example 5 of Optical Functional Device 700>

The optical functional device 700 of one embodiment of the present invention includes the driver circuit RD, a conductive film RS(i), a conductive film TX(i), and a conductive film SE(i) (see FIG. 4 and FIG. 6).

«Configuration Example of Driver Circuit RD»

The driver circuit RD supplies a third selection signal, a fourth selection signal, and a fifth selection signal.

The conductive film RS(i) is supplied with the third selection signal, the conductive film TX(i) is supplied with the fourth selection signal, and the conductive film SE(i) is supplied with the fifth selection signal.

«Configuration Example 1 of Pixel Circuit 530S(i,j)»

The pixel circuit 530S(i,j) is electrically connected to the conductive film RS(i), the conductive film TX(i), and the conductive film SE(i). The conductive film RS(i) supplies the third selection signal, the conductive film TX(i) supplies the fourth selection signal, and the conductive film SE(i) supplies the fifth selection signal.

The pixel circuit 530S(i,j) is initialized in response to the third selection signal, performs image capturing in response to the fourth selection signal, and supplies an imaging signal in response to the fifth selection signal. Image capturing can be performed in a period during which the light-emitting device 550X(i,j) emits light.

«Configuration Example 2 of Pixel Circuit 530S(i,j)»

The pixel circuit 530S(i,j) includes a switch SW31, a switch SW32, a switch SW33, a transistor M31, a capacitor C31, and a node FD.

The switch SW31 includes a first terminal electrically connected to the photoelectric conversion device 550S(i,j), a second terminal electrically connected to the node FD, and a gate electrode having a function of controlling an on/off state of the switch SW31 according to the potential of a conductive film TX(i).

The switch SW32 includes a first terminal electrically connected to the node FD, a second terminal electrically connected to a conductive film VR, and a gate electrode having a function of controlling an on/off state of the switch SW32 according to the potential of the conductive film RS(i).

The capacitor C31 includes a conductive film electrically connected to the node FD and a conductive film electrically connected to a conductive film VCP.

The transistor M31 includes a gate electrode electrically connected to the node FD and a first electrode electrically connected to a conductive film VPI.

The switch SW33 includes a first terminal electrically connected to a second electrode of the transistor M31, a second terminal electrically connected to the conductive film WX(j), and a gate electrode having a function of controlling an on/off state of the switch SW33 according to the potential of the conductive film SE(i).

Accordingly, an imaging signal generated by the photoelectric conversion device 550S(i,j) can be transferred to the node FD using the switch SW31. Alternatively, an imaging signal generated by the photoelectric conversion device 550S(i,j) can be stored in the node FD using the switch SW31. Alternatively, electrical continuity between the pixel circuit 530S(i,j) and the photoelectric conversion device 550S(i,j) can be broken by the switch SW31. Alternatively, a correlated double sampling method can be used. Alternatively, noise in an imaging signal can be reduced. As a result, a novel device that is highly convenient, useful, or reliable can be provided.

<Structure Example 6 of Optical Functional Device 700>

The optical functional device 700 of one embodiment of the present invention includes the driver circuit RC, a conductive film CL, and a conductive film CAPSEL (see FIG. 4 and FIGS. 7A and 7B).

The optical functional device 700 also includes a conductive film VLEN and a conductive film VIV.

The optical functional device 700 also includes a conductive film VCL, a conductive film CDSVDD, a conductive film CDSVSS, and a conductive film CDSBIAS.

«Configuration Example of Driver Circuit RC»

The drive circuit RC includes a read circuit RC(j) (see FIG. 4). The read circuit RC(j) includes an amplifier circuit AMP1($j$) and the sampling circuit SC(j).

[Configuration Example 1 of Amplifier Circuit AMP1($j$)]

The amplifier circuit AMP1($j$) is electrically connected to the conductive film WX(j) and has a function of amplifying an imaging signal.

[Configuration Example 2 of amplifier circuit AMP1($j$)]

The amplifier circuit AMP1($j$) includes a transistor M32($j$) including a gate electrode electrically connected to the conductive film VLEN, a first electrode electrically connected to the conductive film WX(j), and a second electrode electrically connected to the conductive film VIV.

The conductive film WX(j) connects the transistor M31 and the transistor M32($j$) when the switch SW33 is in an on state (see FIG. 6 and FIG. 7A). Thus, a source follower circuit can be configured with the transistor M31 and the transistor M32($j$). Alternatively, the potential of the conductive film WX(j) can be changed according to the potential of the node FD.

[Configuration Example of Sampling Circuit SC(j)]

The sampling circuit SC(j) includes a terminal IN1($j$), a terminal IN2, a terminal IN3, and a terminal OUT(j) (see FIG. 7B).

The terminal IN1($j$) is electrically connected to the conductive film WX(j), the terminal IN2 is electrically connected to the conductive film CL, and the terminal IN3 is electrically connected to the conductive film CAPSEL.

The sampling circuit SC(j) has a function of obtaining an imaging signal according to the potentials of the conductive film CL and the conductive film CAPSEL. The terminal OUT(j) has a function of supplying a signal which changes according to the potential of the terminal IN1(j).

Accordingly, an imaging signal can be obtained from the pixel circuit 530S(i,j). Alternatively, a correlated double sampling method can be employed, for example. Alternatively, the sampling circuit SC(j) can be provided for each conductive film WX(j). Alternatively, a differential signal of the pixel circuit 530S(i,j) can be obtained by the corresponding conductive film WX(j). Alternatively, the operating frequency of the sampling circuit SC(j) can be low. Alternatively, noise can be reduced. As a result, a novel device that is highly convenient, useful, or reliable can be provided.

<Structure Example 7 of Optical Functional Device 700>

The optical functional device 700 of one embodiment of the present invention includes the region 231 (see FIG. 4). The display region 231 has a function of displaying an image.

The region 231 includes a group of pixels 703(i,1) to 703(i,n) and another group of pixels 703(1,j) to 703(m,j).

The group of pixels 703(i,1) to 703(i,n) are arranged in the row direction (the direction indicated by the arrow R1 in FIG. 4) and include the pixel 703(i,j).

The conductive film G1(i) is electrically connected to the group of pixels 703(i,1) to 703(i,n).

The another group of pixels 703(1,j) to 703(m,j) are arranged in the column direction intersecting the row direction (the direction indicated by the arrow C1 in FIG. 4) and include the pixel 703(i,j).

The another group of pixels 703(1,j) to 703(m,j) is electrically connected to the conductive film S1(j).

<Structure Example 8 of Optical Functional Device 700>

The optical functional device 700 of one embodiment of the present invention includes a multiplexer MUX, an amplifier circuit AMP2, and an analog-to-digital converter circuit ADC (see FIG. 4).

The multiplexer MUX has a function of obtaining an imaging signal from one selected from a plurality of sampling circuits SC(j) and supplying the imaging signal to the amplifier circuit AMP2, for example.

Thus, imaging data can be obtained by selecting a given pixel from a plurality of pixels arranged in the row direction. Alternatively, the number of imaging signals obtained at the same time can be limited to a predetermined number. Alternatively, it is possible to use the analog-to-digital converter circuit ADC in which the number of input channels is smaller than the number of pixels arranged in the row direction. As a result, a novel device that is highly convenient, useful, or reliable can be provided.

The amplifier circuit AMP2 can amplify an imaging signal and supply the amplified signal to the analog-to-digital converter circuit ADC.

Note that this embodiment can be combined with any of the other embodiments in this specification as appropriate.

EXAMPLE 1

In this example, devices 1 to 4 of one embodiment of the present invention will be described with reference to FIG. 8 and FIG. 11 to FIG. 13.

Figure 8:
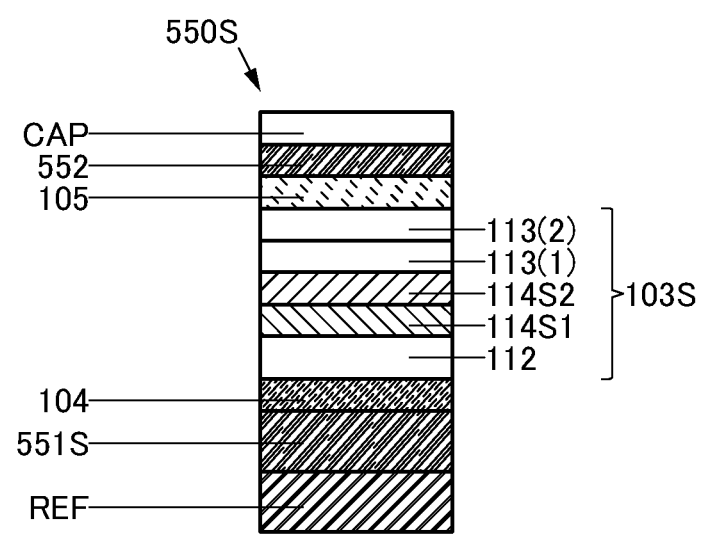
FIG. 8 illustrates a structure of a photoelectric conversion device of Example of the present invention.

FIG. 8 illustrates the structure of the photoelectric conversion device 550S.

Figure 11:
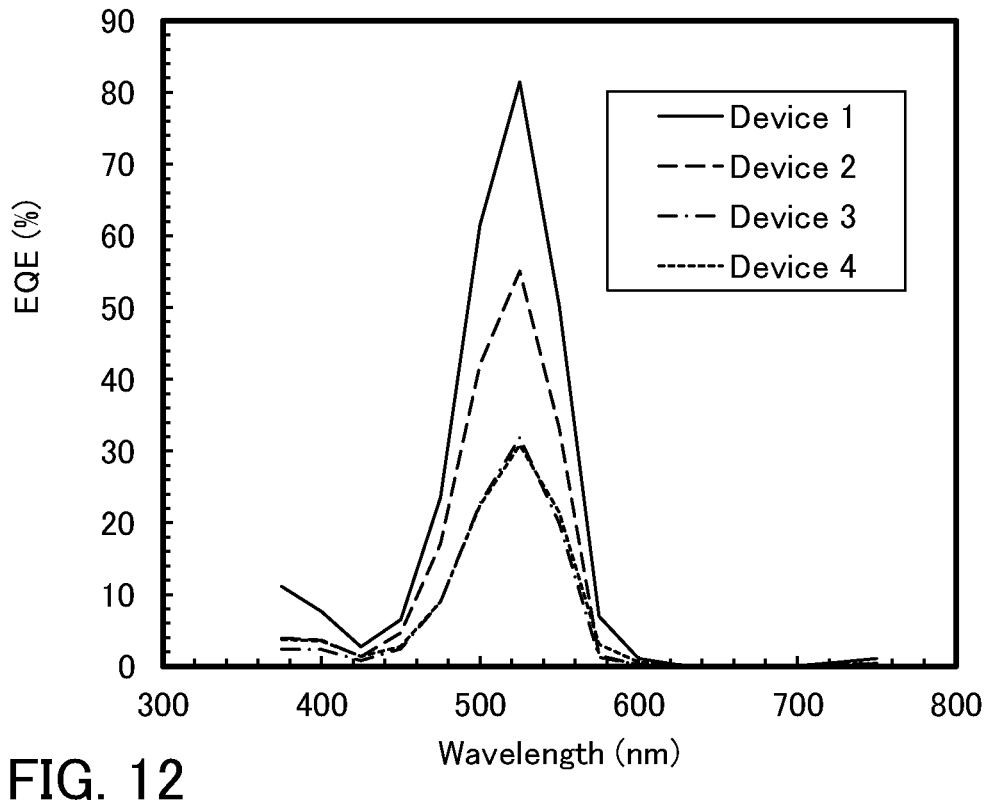
FIG. 11 is a graph showing the characteristics of a photoelectric conversion device fabricated in Example of the present invention.

FIG. 11 shows the spectral sensitivities of the devices 1 to 4.

Figure 12:
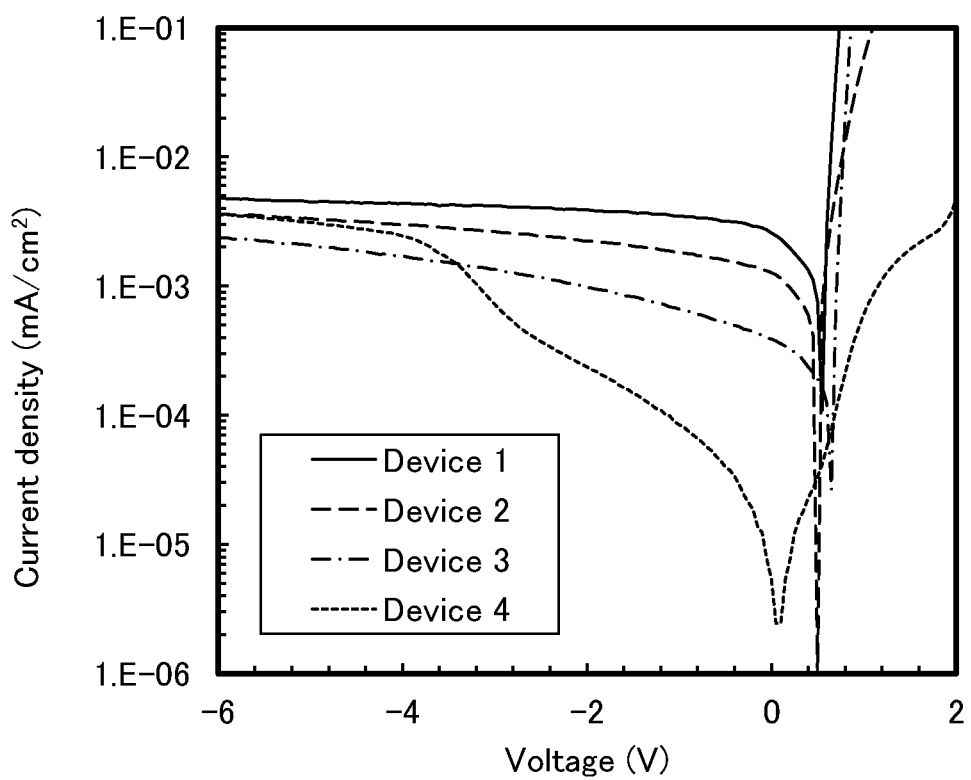
FIG. 12 is a graph showing the characteristics of a photoelectric conversion device fabricated in Example of the present invention.

FIG. 12 shows the voltage-current density characteristics of the devices 1 to 4 in the state of being irradiated with light.

Figure 13:
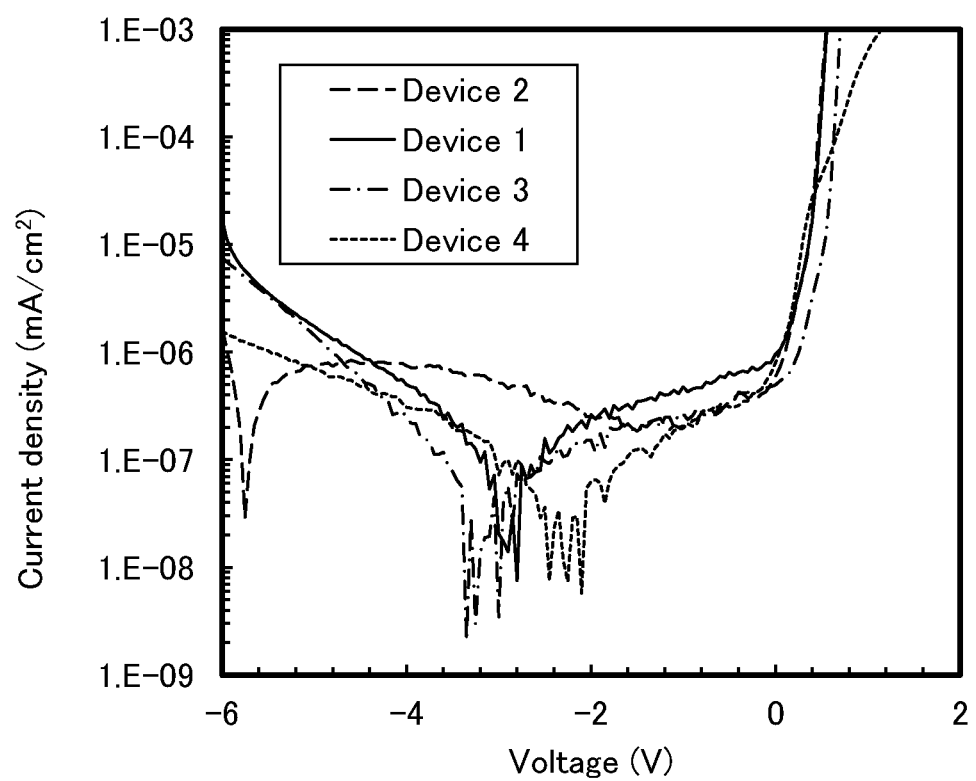
FIG. 13 is a graph showing the characteristics of a photoelectric conversion device fabricated in Example of the present invention.

FIG. 13 shows the voltage-current density characteristics of the devices 1 to 4 in the state of not being irradiated with light.

<Device 1>

The fabricated device 1, which will be described in this example, has a structure similar to that of the photoelectric conversion device 550S (see FIG. 8).

The photoelectric conversion device 550S includes the electrode 551S, the electrode 552, and the unit 103S. The unit 103S is located between the electrode 551S and the electrode 552.

The unit 103S includes the electron-donating material DM1 and the electron-accepting material AM1. The electron-donating material DM1 is a condensed aromatic compound, and the electron-accepting material AM1 has a perylene skeleton and two or more alkyl groups. The alkyl groups each independently have carbon atoms whose number is greater than or equal to 1 and less than or equal to 13.

«Structure of Device 1»

Table 1 shows the structure of the device 1. The structural formulae of materials used in the device described in this example are shown below.

TABLE 1

| Structure | Reference symbol | Material | Composition ratio | Thickness/ nm |
| --- | --- | --- | --- | --- |
| Layer | CAP | DBT3P-II | | 80 |
| Electrode | 552 | Ag:Mg | 1:0.1 | 10 |
| Layer | 105 | LiF | | 1 |
| Layer | 113(2) | NBPhen | | 10 |
| Layer | 113(1) | 2mDBTBPDBq-II | | 10 |
| Layer | 114S2 | Me-PTCDI | | 6 |
| Layer | 114S1 | Rubrene | | 54 |
| Layer | 112 | BBABnf | | 40 |
| Layer | 104 | BBABnf:OCHD-003 | 1:0.1 | 11 |
| Electrode | 551S | ITSO | | 100 |
| Reflective film | REF | APC | | 100 |

TABLE 1-continued
| Structure | Reference symbol | Material | Composition ratio | Thickness/ nm |
| --- | --- | --- | --- | --- |
[Chemical Formula 7]
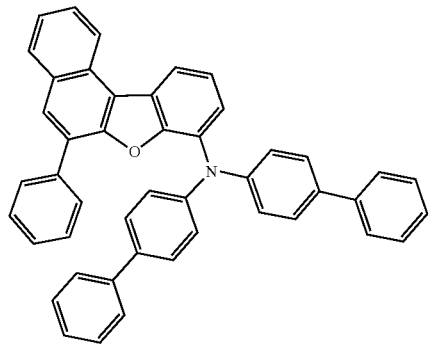
BBaBnf
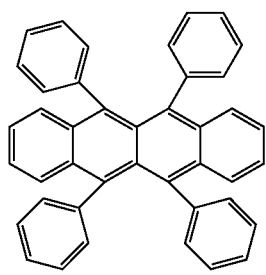
Rubrene
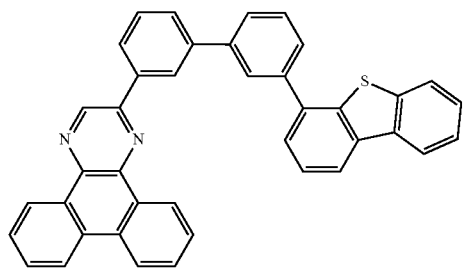
2mDBTBPDBq-II
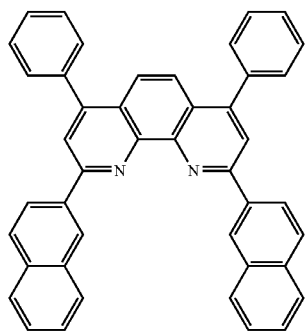
NBPhen TABLE 1-continued

| Structure | Reference symbol | Material | Composition ratio | Thickness/ nm |
|---|---|---|---|---|

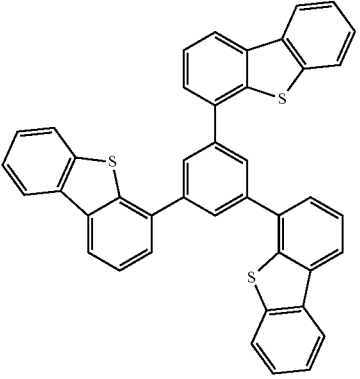
DBT3P-II

[Chemical Formula 8]

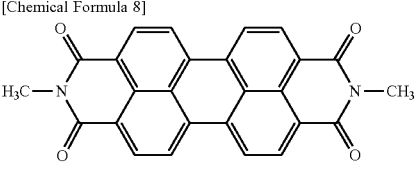
Me-PTCDI

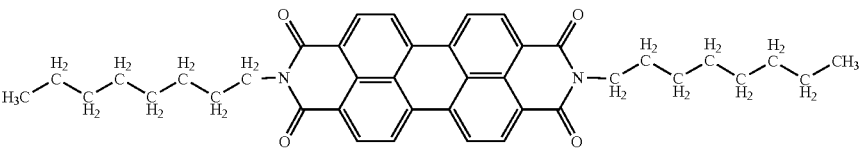
PTCDI-C8

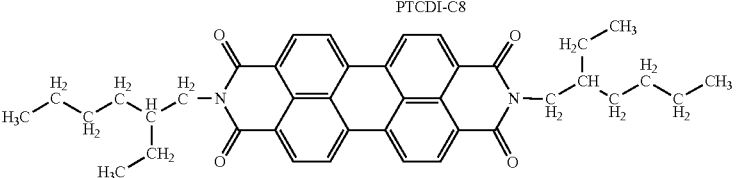
EtHex-PTCDI

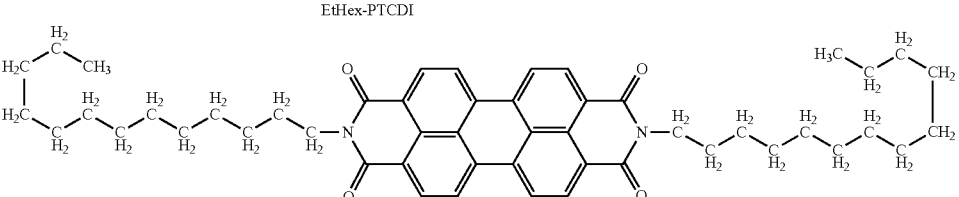
PTCDI-C13

«Fabrication Method for Device 1»

The device 1 described in this example was fabricated using a method including the following steps.

[First Step]

A reflective film REF was formed in the first step. Specifically, the reflective film REF was formed by a sputtering method using an alloy containing silver (Ag), palladium (Pd), and copper (Cu) (abbreviation: APC) as a target.

The reflective film REF contains APC and has a thickness of 100 nm.

[Second Step]

In the second step, the electrode 551S was formed over the reflective film REF. Specifically, the electrode 551S was formed by a sputtering method using indium oxide-tin oxide containing silicon or silicon oxide (abbreviation: ITSO) as a target.

The electrode 551S contains ITSO and has a thickness of 100 nm and an area of 4 mm² (2 mm×2 mm).

Next, a substrate over which the electrode 551S was formed was washed with water, and baking was performed at 200° C. for 1 hour. Then, the substrate was transferred into a vacuum evaporation apparatus where the pressure was reduced to approximately $10^{-4}$ Pa, and vacuum baking was performed at 180° C. for 60 minutes in a heating chamber of the vacuum evaporation apparatus. Then, the substrate was naturally cooled to room temperature.

[Third Step]

In the third step, the layer 104 was formed over the electrode 551S. Specifically, materials of the layer 104 were co-deposited by a resistance-heating method.

The layer 104 has a thickness of 11 nm and contains N,N-bis(4-biphenyl)-6-phenylbenzo[b]naphtho[1,2-d]furan-8-amine (abbreviation: BBABnf) and an electron acceptor material (OCHD-003) at a weight ratio of BBABnf: OCHD-003=1:0.1. The electron acceptor material OCHD-003 contains fluorine and the molecular weight thereof is 672.

[Fourth Step]

In the fourth step, the layer 112 was formed over the layer 104. Specifically, a material of the layer 112 was deposited by a resistance-heating method.

The layer 112 contains BBABnf and has a thickness of 40 nm.

[Fifth Step]

In the fifth step, the layer 114S1 was formed over the layer 112. Specifically, a material of the layer 114S1 was deposited by a resistance-heating method. The layer 114S1 contains rubrene and has a thickness of 54 nm.

[Sixth Step]

In the sixth step, the layer 114S2 was formed over the layer 114S1. Specifically, a material of the layer 114S2 was deposited by a resistance-heating method. The layer 114S2 contains Me-PTCDI and has a thickness of 6 nm.

[Seventh Step]

In the seventh step, a layer 113(1) was formed over the layer 114S2. Specifically, a material of the layer 113(1) was deposited by a resistance-heating method.

The layer 113(1) contains 2mDBTBPDBq-II and has a thickness of 10 nm.

[Eighth Step]

In the eighth step, a layer 113(2) was formed over the layer 113(1). Specifically, a material of the layer 113(2) was deposited by a resistance-heating method. The layer 113(2) includes 2,9-di(2-naphthyl)-4,7-diphenyl-1,10-phenanthroline (abbreviation: NBPhen) and has a thickness of 10 nm.

[Ninth Step]

In the ninth step, the layer 105 was formed over the layer 113(2). Specifically, a material of the layer 105 was deposited by a resistance-heating method.

The layer 105 contains lithium fluoride (abbreviation: LiF) and has a thickness of 1 nm.

[Tenth Step]

In the tenth step, the electrode 552 was formed over the layer 105. Specifically, materials of the electrode 552 were co-deposited by a resistance-heating method.

The electrode 552 has a thickness of 10 nm and contains silver (Ag) and magnesium (Mg) at a volume ratio of Ag:Mg=1:0.1.

[Eleventh Step]

In the eleventh step, a layer CAP was formed over the electrode 552. Specifically, a material of the layer CAP was deposited by a resistance-heating method. The layer CAP contains 4,4',4''-(benzene-1,3,5-triyl)tri(dibenzothiophene) (abbreviation: DBT3P-II) and has a thickness of 80 nm.

«Operation Characteristics of Device 1»

The operation characteristics of the device 1 were measured at room temperature (see FIG. 11 to FIG. 13). Monochromatic light was emitted in the state where a potential of −4 V relative to the potential of the electrode 551S was supplied to the electrode 552, and the light-to-current conversion efficiency with respect to the amount of irradiation light was measured as EQE (see FIG. 11). Monochromatic light was emitted at intervals of 25 nm in the wavelength range from 375 nm to 750 nm. The potential of the electrode 551S from −6 V to +2 V relative to the potential of the electrode 552 was swept in the state where light with a wavelength of 525 nm was emitted with an intensity of 12.5 $\mu W/cm^2$, and the density of current flowing through the device was measured (see FIG. 12). In addition, the potential of the electrode 551S from −6 V to +2 V relative to the potential of the electrode 552 was swept in the state where no light was emitted, and the density of dark current flowing through the device was measured (see FIG. 13). Table 2 shows the characteristics of the device 1 and the other devices to be described later.

TABLE 2

|  | Electron-accepting material AM1 | EQE (%) |
| --- | --- | --- |
| Device 1 | Me-PTCDI | 81 |
| Device 2 | PTCDI-C8 | 55 |
| Device 3 | PTCDI-C13 | 31 |
| Device 4 | EtHex-PTCDI | 30.8 |

The device 1 was found to have favorable characteristics. For example, the device 1 has favorable current saturation characteristics and high efficiency. An imaging device also suitable for capturing images of subjects with an analog gray scale was provided.

<Device 2>

The fabricated device 2, which will be described in this example, has a structure similar to that of the photoelectric conversion device 550S (see FIG. 8). The device 2 differs from the device 1 in that the layer 114S2 contains PTCDI-C8 instead of Me-PTCDI.

«Fabrication Method for Device 2»

A fabrication method for the device 2 differs from the fabrication method for the device 1 in that in the sixth step, the layer 114S2 with a thickness of 6 nm was formed over the layer 114S1 with the use of PTCDI-C8.

<Device 3>

The fabricated device 3, which will be described in this example, has a structure similar to that of the photoelectric conversion device 550S (see FIG. 8). The device 3 differs from the device 1 in that the layer 114S2 contains PTCDI-C13 instead of Me-PTCDI.

«Fabrication method for device 3»

A fabrication method for the device 3 differs from the fabrication method for the device 1 in that in the sixth step, the layer 114S2 with a thickness of 6 nm was formed over the layer 114S1 with the use of PTCDI-C13.

<Device 4>

The fabricated device 4, which will be described in this example, has a structure similar to that of the photoelectric conversion device 550S (see FIG. 8). The device 4 differs from the device 1 in that the layer 114S2 contains EtHex-PTCDI instead of Me-PTCDI.

«Fabrication Method for Device 4»

A fabrication method for the device 4 differs from the fabrication method for the device 1 in that in the sixth step, the layer 114S2 with a thickness of 6 nm was formed over the layer 114S1 with the use of EtHex-PTCDI.

EXAMPLE 2

In this example, the solubilities of electron-accepting materials that can be used for the photoelectric conversion device of one embodiment of the present invention will be described. The solubilities of the materials were measured using a liquid chromatography mass spectrometer.

Specifically, the case where a peak of the chromatogram and the MS spectrum of a material were detected using the liquid chromatography mass spectrometer is indicated with a circle. The case where no peak of the chromatogram of a material was detected but the MS spectrum thereof was detected is indicated with a triangle. The case where neither a peak of the chromatogram of a material nor the MS spectrum thereof was detected is indicated with a cross.

The liquid chromatography mass spectrometer is constructed of ACQUITY H-Class (produced by Waters Corporation) and Xevo™ G2 Q-TOF MS (produced by Waters Corporation), and ACQUITY UPLC (registered trademark) BEH C8 Column (1.7 μm, 2.1×100 mm) (produced by Waters Corporation, hereinafter referred to as Column) was used as a column.

A method for preparing a sample used for the solubility measurement will be described. In a reagent bottle made of glass were put 0.5 mg of the electron-accepting material AM1 and 0.25 mL of chloroform, and ultrasonic treatment was performed for 1 minute. To the obtained mixture was added 2.5 mL of acetonitrile, and the resulting mixture was left still. After 18 hours, the resulting mixture was filtrated. As a sample (filtrate), a solution with the color of AM1 was obtained in the case where AM1 was dissolved therein (an orange solution, for the sample of this example), and a colorless and transparent sample was obtained in the case where the solubility was low. With the use of the obtained filtrate as a sample, a solubility test was performed using the liquid chromatography mass spectrometer.

A measurement method for the solubility test using the liquid chromatography mass spectrometer will be described. As a mobile phase A and a mobile phase B, acetonitrile and a formic acid aqueous solution (0.1%) were used, respectively, the velocity of flow of a solvent was 0.5 mL/min, and the injection amount of the sample was 5 μL.

«Solubility Test for Me-PTCDI»

As a result of preparing a sample of Me-PTCDI, the sample was colorless and transparent; thus, a solubility test was not performed, determining that Me-PTCDI was not dissolved at all. The result of a solubility test was determined as a cross.

«Solubility Test for PTCDI-C8»

A sample of PTCDI-C8 was an orange solution, and solution sending in the measurement was performed under the condition that the ratio of the mobile phase A to the mobile phase B has a linear gradient such that it was 75:25 for 1 minute from the start of the measurement and was 95:5 after 1 minute passed until 9 more minutes passed.

«Solubility Test for PTCDI-C13»

A sample of PTCDI-C13 was a pale-orange solution, and solution sending in the measurement was performed under the condition that the ratio of the mobile phase A to the mobile phase B has a linear gradient such that it was 80:20 for 1 minute from the start of the measurement and was 95:5 after 1 minute passed until 9 more minutes passed.

«Solubility Test for EtHex-PTCDI»A sample of EtHex-PTCDI was an orange solution, and solution sending in the measurement was performed under the condition that the ratio of the mobile phase A to the mobile phase B was kept at 95:5 for 10 minutes from the start of the measurement.

«Solubilities of Materials»

Table 3 lists the solubilities of the materials.

TABLE 3

| Electron-accepting material AM1 | Solubility |
|---|---|
| Me-PTCDI | X |
| PTCDI-C8 | Δ |
| PTCDI-C13 | X |
| EtHex-PTCDI | ○ |

Both PTCDI-C8 and EtHex-PTCDI were found to have favorable solubility compared with Me-PTCDI and PTCDI-C13. This indicates that an alkyl group having 2 to 12 carbon atoms has an effect of improving the solubility of a perylenetetracarboxylic diimide derivative. In addition, EtHex-PTCDI having 8 carbon atoms had higher solubility than PTCDI-C8 having 8 carbon atoms. This indicates that a branched alkyl group has a higher effect of improving the solubility of a perylenetetracarboxylic diimide derivative than a chain alkyl group.

EXAMPLE 3

In this example, devices D111 to D411 of embodiments of the present invention will be described with reference to FIG. 9 to FIG. 25.

Figure 9:
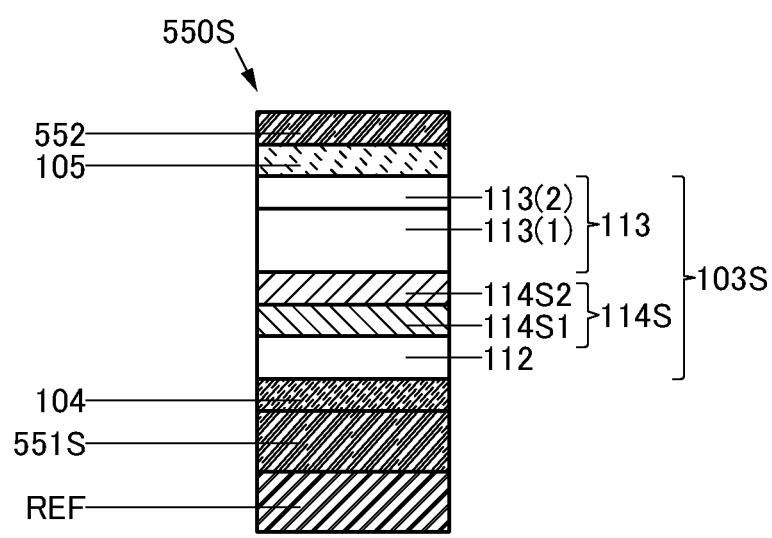
FIG. 9 illustrates a structure of a photoelectric conversion device of Example of the present invention.

FIG. 9 illustrates a structure of the photoelectric conversion device 550S.

Figure 10:
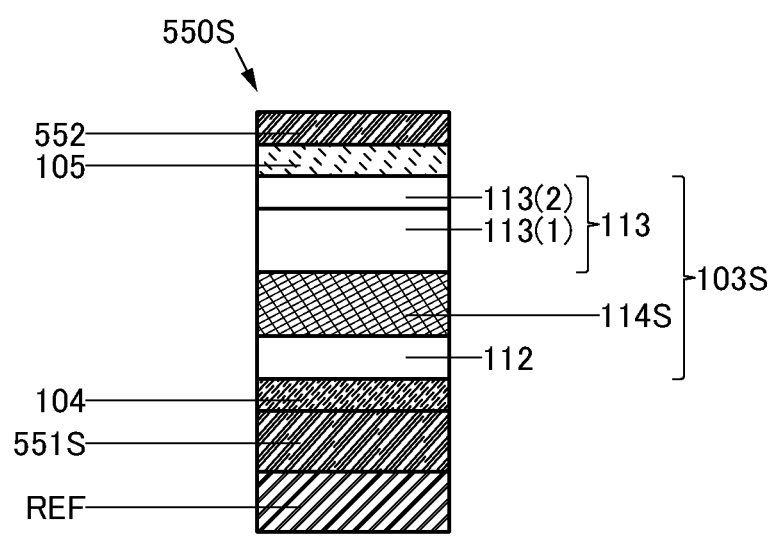
FIG. 10 illustrates a structure of a photoelectric conversion device of Example of the present invention.

FIG. 10 illustrates a structure of the photoelectric conversion device 550S.

Figure 14:
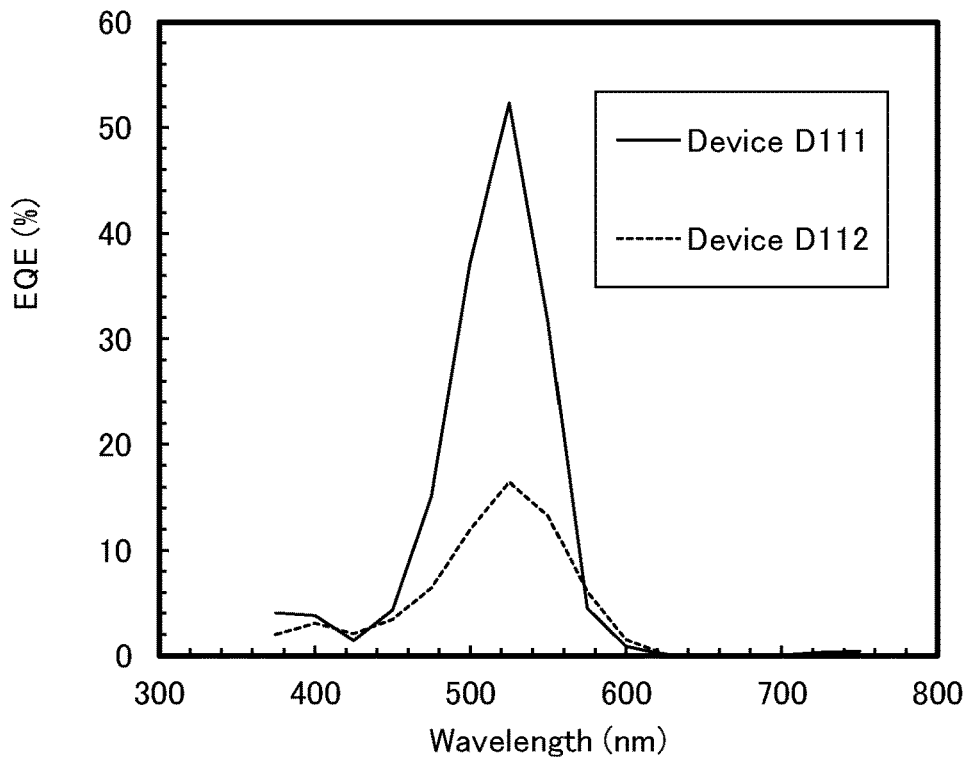
FIG. 14 is a graph showing the characteristics of a photoelectric conversion device fabricated in Example of the present invention.

FIG. 14 shows the spectral sensitivities of the device D111 and the device D112.

Figure 15:
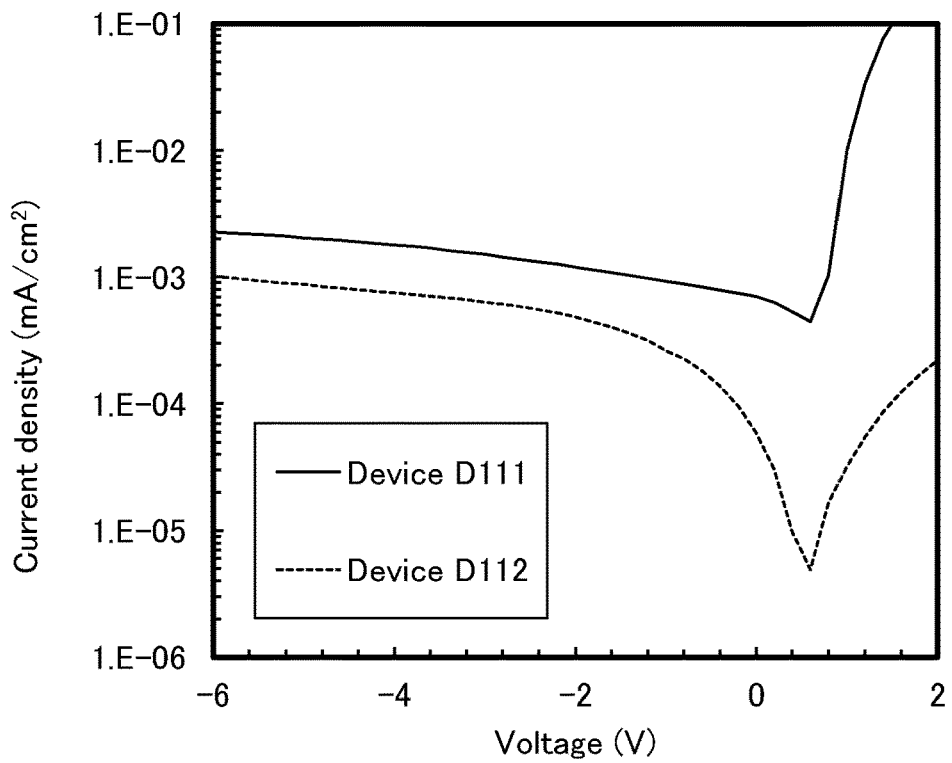
FIG. 15 is a graph showing the characteristics of a photoelectric conversion device fabricated in Example of the present invention.

FIG. 15 shows the voltage-current density characteristics of the device D111 and the device D112 in the state of being irradiated with light.

Figure 16:
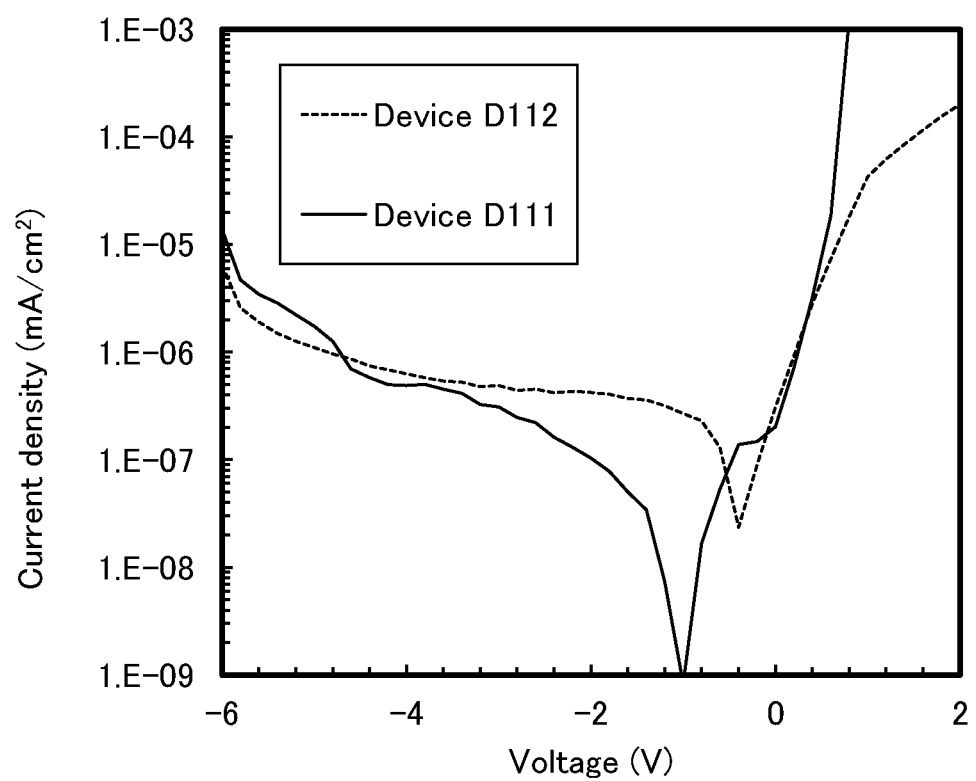
FIG. 16 is a graph showing the characteristics of a photoelectric conversion device fabricated in Example of the present invention.

FIG. 16 shows the voltage-current density characteristics of the device D111 and the device D112 in the state of not being irradiated with light.

Figure 17:
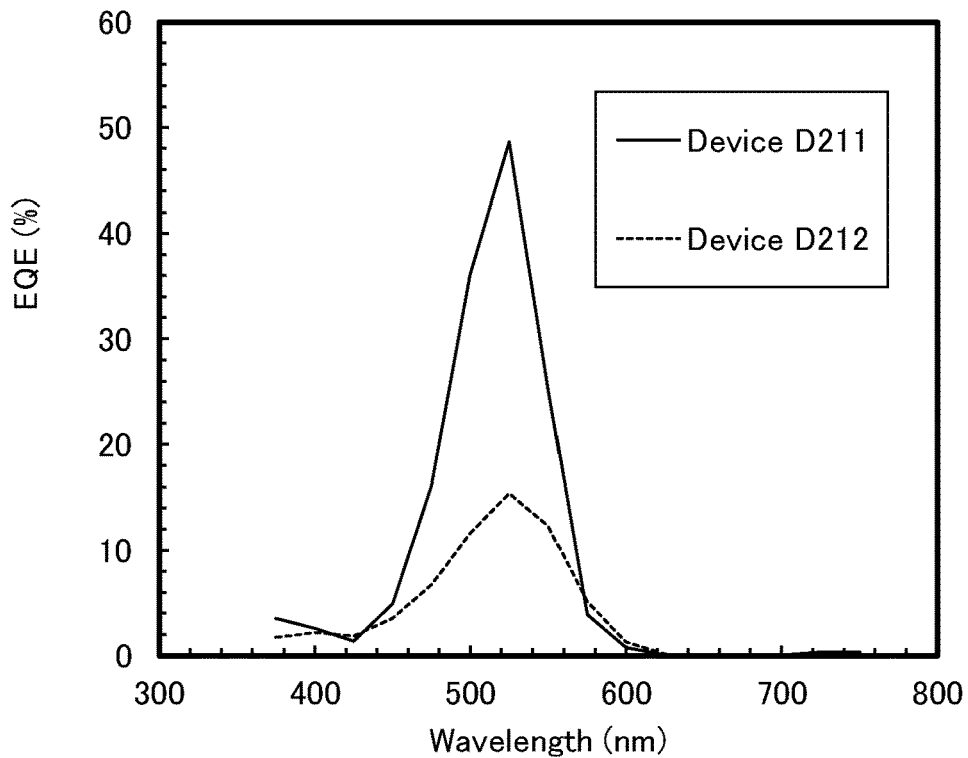
FIG. 17 is a graph showing the characteristics of a photoelectric conversion device fabricated in Example of the present invention.

FIG. 17 shows the spectral sensitivities of the device D211 and the device D212.

Figure 18:
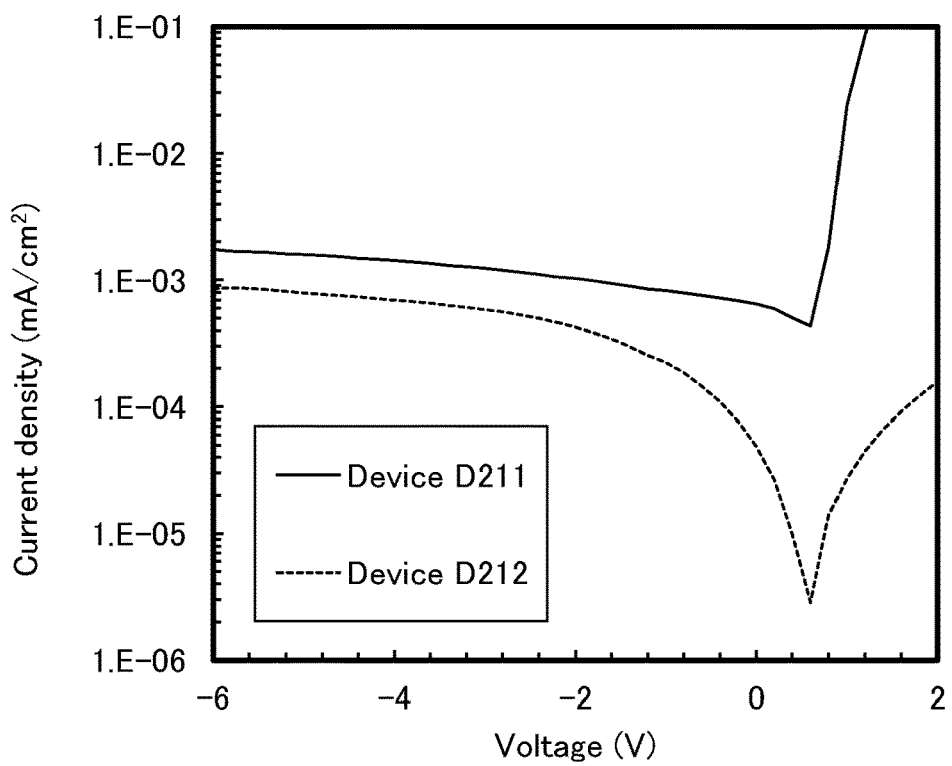
FIG. 18 is a graph showing the characteristics of a photoelectric conversion device fabricated in Example of the present invention.

FIG. 18 shows the voltage-current density characteristics of the device D211 and the device D212 in the state of being irradiated with light.

Figure 19:
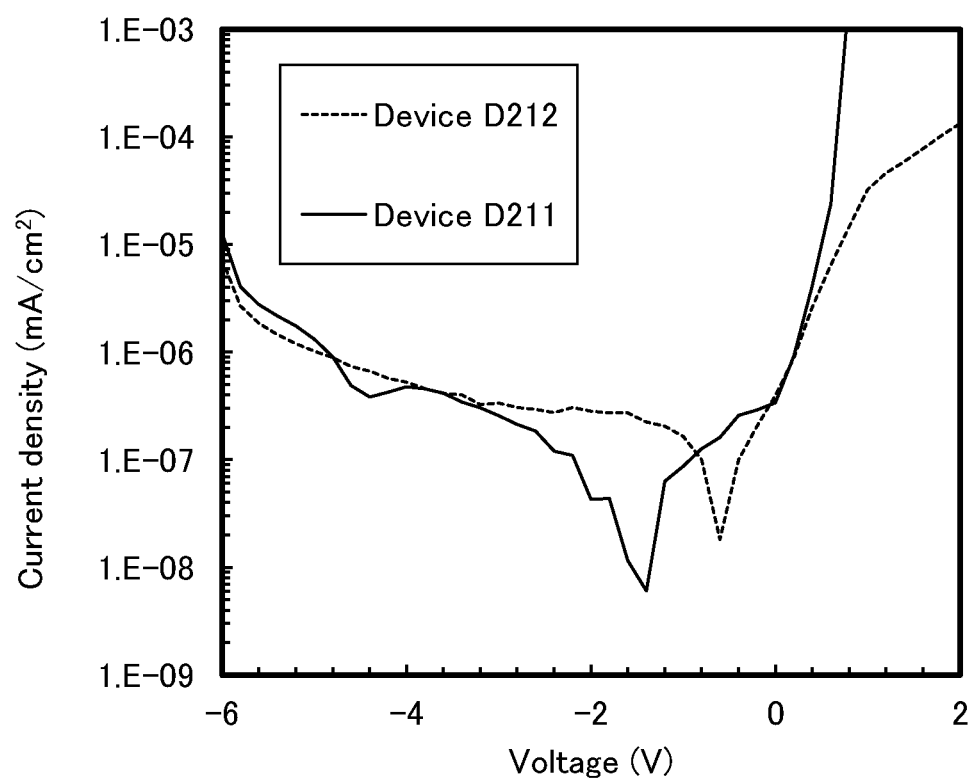
FIG. 19 is a graph showing the characteristics of a photoelectric conversion device fabricated in Example of the present invention.

FIG. 19 shows the voltage-current density characteristics of the device D211 and the device D212 in the state of not being irradiated with light.

Figure 20:
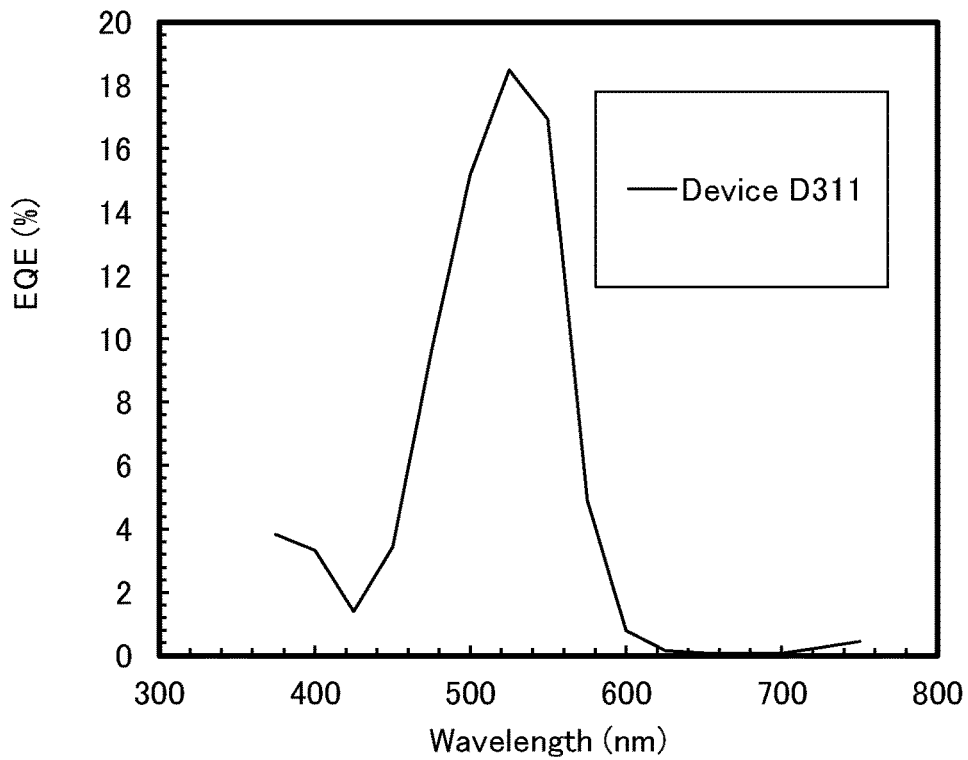
FIG. 20 is a graph showing the characteristics of a photoelectric conversion device fabricated in Example of the present invention.

FIG. 20 shows the spectral sensitivity of the device D311.

Figure 21:
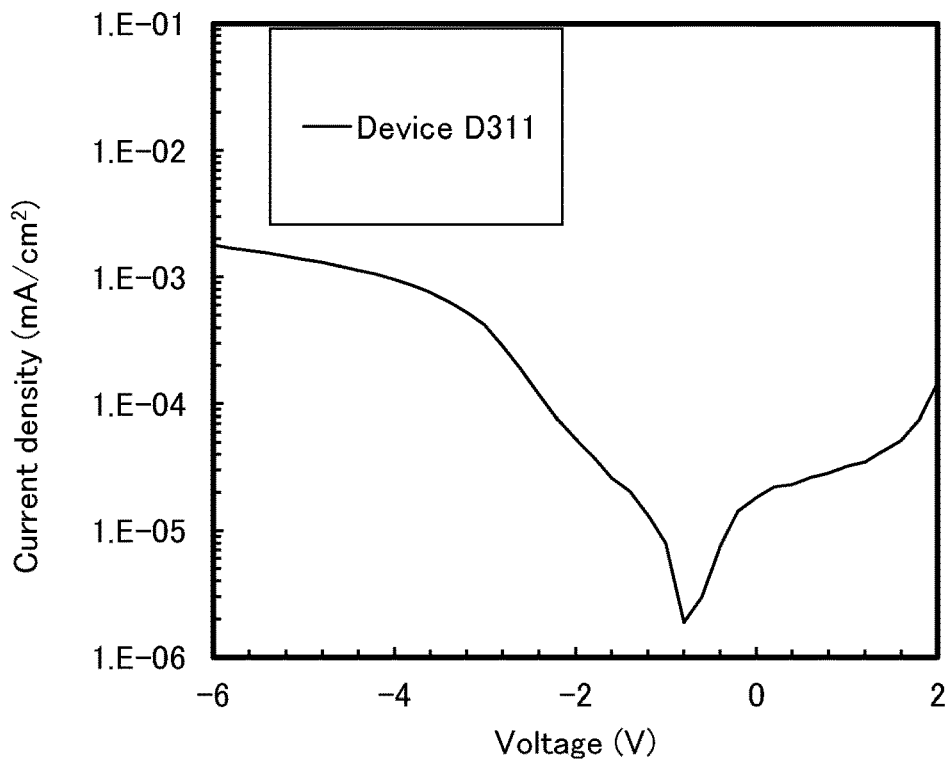
FIG. 21 is a graph showing the characteristics of a photoelectric conversion device fabricated in Example of the present invention.

FIG. 21 shows the voltage-current density characteristics of the device D311 in the state of being irradiated with light.

Figure 22:
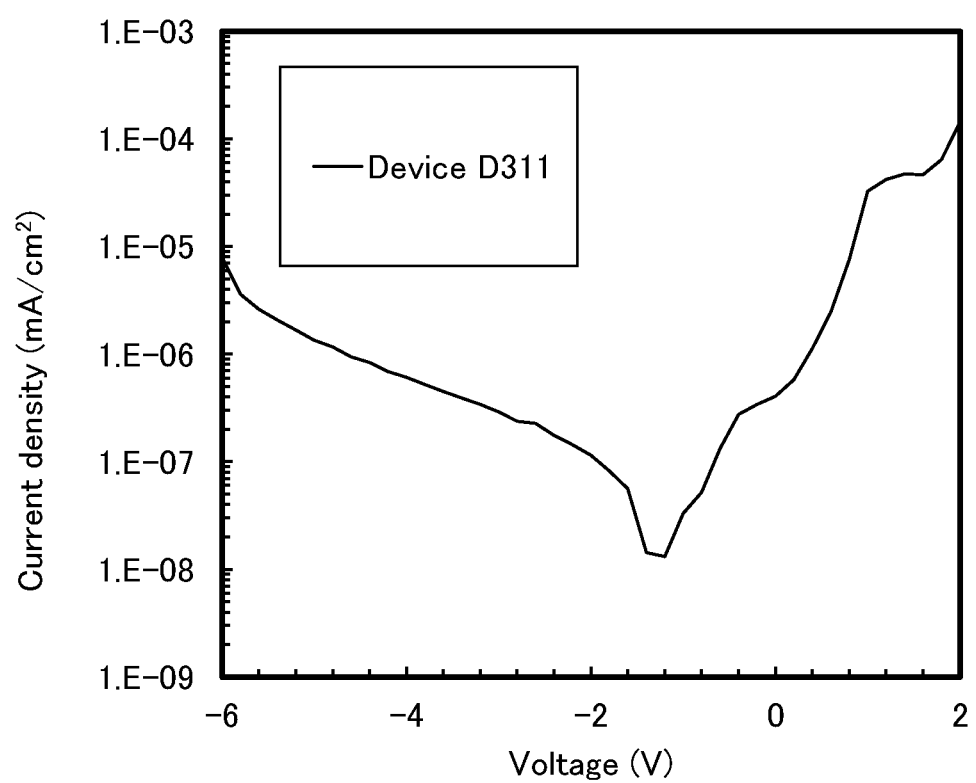
FIG. 22 is a graph showing the characteristics of a photoelectric conversion device fabricated in Example of the present invention.

FIG. 22 shows the voltage-current density characteristics of the device D311 in the state of not being irradiated with light.

Figure 23:
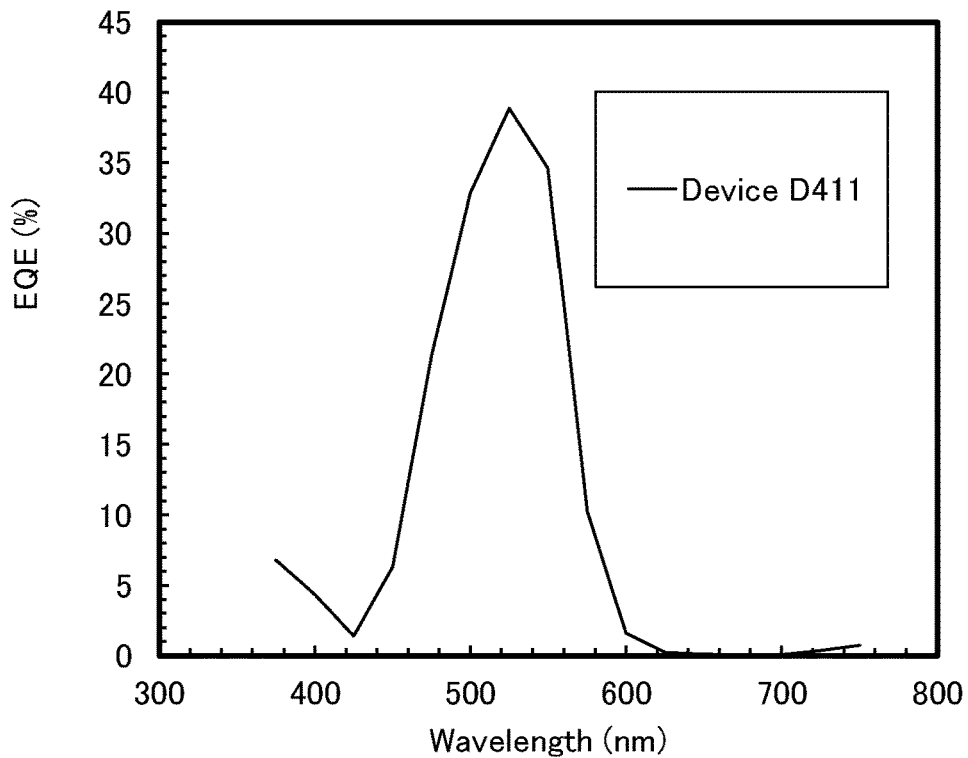
FIG. 23 is a graph showing the characteristics of a photoelectric conversion device fabricated in Example of the present invention.

FIG. 23 shows the spectral sensitivity of the device D411.

Figure 24:
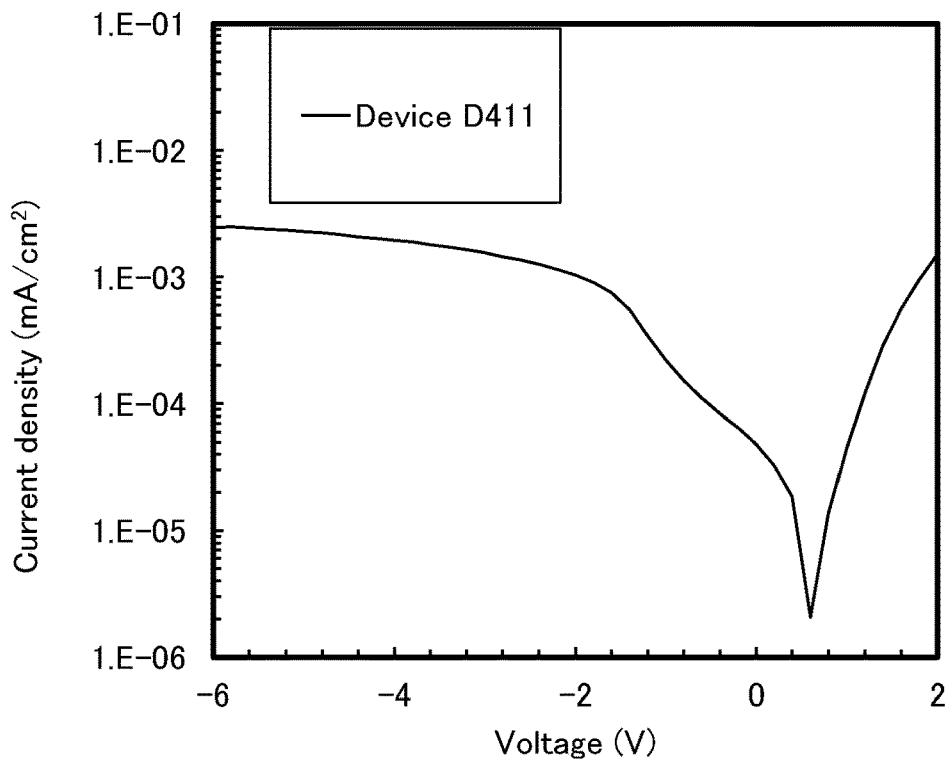
FIG. 24 is a graph showing the characteristics of a photoelectric conversion device fabricated in Example of the present invention.

FIG. 24 shows the voltage-current density characteristics of the device D411 in the state of being irradiated with light.

Figure 25:
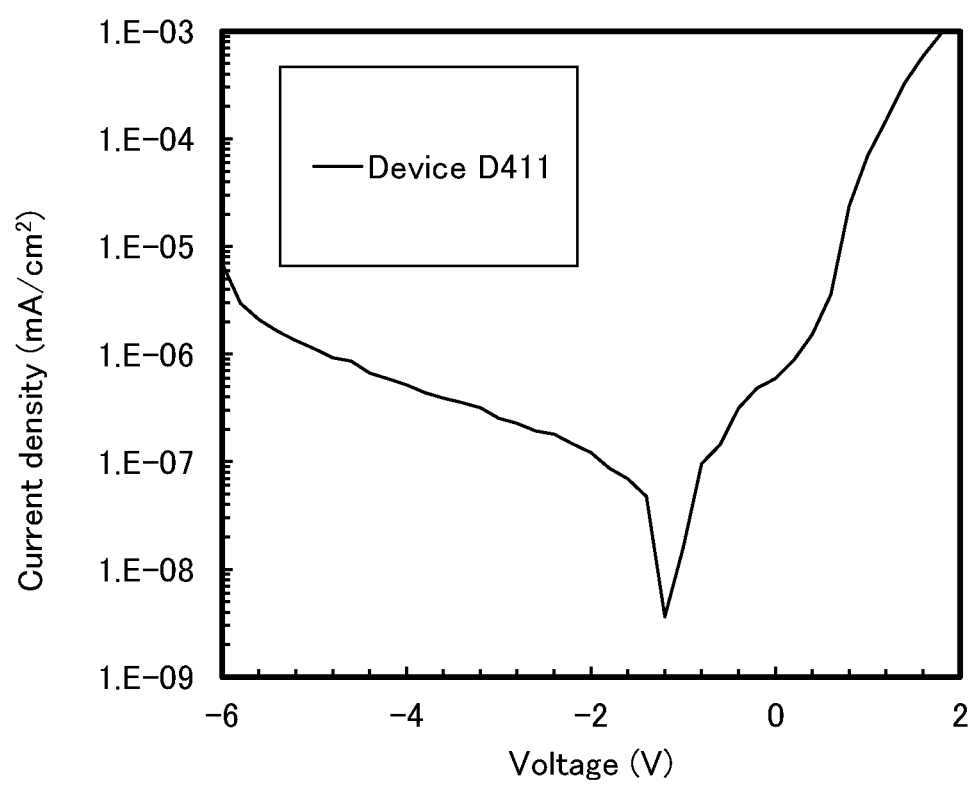
FIG. 25 is a graph showing the characteristics of a photoelectric conversion device fabricated in Example of the present invention.

FIG. 25 shows the voltage-current density characteristics of the device D411 in the state of being not irradiated with light.

<Device D111>

The fabricated device D111, which will be described in this example, has a structure similar to that of the photoelectric conversion device 550S (see FIG. 9).

The photoelectric conversion device 550S includes the electrode 551S, the electrode 552, and the unit 103S. The unit 103S is located between the electrode 551S and the electrode 552.

The unit 103S includes the electron-donating material DM1 and the electron-accepting material AM1. The electron-donating material DM1 is a condensed aromatic compound, and the electron-accepting material AM1 has a perylene skeleton and two or more alkyl groups. The alkyl groups each independently have carbon atoms whose number is greater than or equal to 1 and less than or equal to 13.

«Structures of Device D111 and Device D112»

Table 4 shows the structures of the device D111 and the device D112. Note that y in the table is 10 or 20.

TABLE 4

| Structure | Reference symbol | Material | Composition ratio | Thickness/ nm |
|---|---|---|---|---|
| Electrode | 552 | Ag:Mg | 1:0.1 | 10 |
| Layer | 105 | LiF | | 1 |
| Layer | 113 (2) | NBPhen | | y |
| Layer | 113 (1) | 2mDBTBPDBq-II | | y |
| Layer | 114S2 | EtHex-PTCDI | | 18 |
| Layer | 114S1 | Rubrene | | 42 |
| Layer | 112 | BBABnf | | 40 |
| Layer | 104 | BBABnf:OCHD-003 | 1:0.1 | 11 |
| Electrode | 551S | ITSO | | 100 |
| Reflective film | ReF | APC | | 100 |

«Fabrication Method for Device D111»

The device D111 described in this example was fabricated using a method including the following steps.

[First Step]

A reflective film REF was formed in the first step. Specifically, the reflective film REF was formed by a sputtering method using an alloy containing silver (Ag), palladium (Pd), and copper (Cu) (abbreviation: APC) as a target.

The reflective film REF contains APC and has a thickness of 100 nm.

[Second Step]

In the second step, the electrode 551S was formed over the reflective film REF. Specifically, the electrode 551S was formed by a sputtering method using indium oxide-tin oxide containing silicon or silicon oxide (abbreviation: ITSO) as a target.

The electrode 551S contains ITSO and has a thickness of 100 nm and an area of 4 mm$^2$ (2 mm×2 mm).

Next, a substrate over which the electrode 551S was formed was washed with water, and baking was performed at 200° C. for 1 hour. Then, the substrate was transferred into a vacuum evaporation apparatus where the pressure was reduced to approximately 10$^{-4}$ Pa, and vacuum baking was performed at 180° C. for 60 minutes in a heating chamber of the vacuum evaporation apparatus. Then, the substrate was naturally cooled to room temperature.

[Third Step]

In the third step, the layer 104 was formed over the electrode 551S. Specifically, materials of the layer 104 were co-deposited by a resistance-heating method.

The layer 104 has a thickness of 11 nm and contains BBABnf and OCHD-003 at a weight ratio of BBABnf: OCHD-003=1:0.1.

[Fourth Step]

In the fourth step, the layer 112 was formed over the layer 104. Specifically, a material of the layer 112 was deposited by a resistance-heating method.

The layer 112 contains BBABnf and has a thickness of 40 nm.

[Fifth Step]

In the fifth step, the layer 114S1 was formed over the layer 112. Specifically, a material of the layer 114S1 was deposited by a resistance-heating method.

The layer 114S1 contains rubrene and has a thickness of 42 nm.

[Sixth Step]

In the sixth step, the layer 114S2 was formed over the layer 114S1. Specifically, a material of the layer 114S2 was deposited by a resistance-heating method.

The layer 114S2 contains EtHex-PTCDI and has a thickness of 18 nm.

[Seventh Step]

In the seventh step, the layer 113(1) was formed over the layer 114S2. Specifically, a material of the layer 113(1) was deposited by a resistance-heating method.

The layer 113(1) contains 2mDBTBPDBq-II and has a thickness of 10 nm.

[Eighth Step]

In the eighth step, a layer 113(2) was formed over the layer 113(1). Specifically, a material of the layer 113(2) was deposited by a resistance-heating method.

Note that the layer 113(2) contains NBPhen and has a thickness of 10 nm.

[Ninth Step]

In the ninth step, the layer 105 was formed over the layer 113(2). Specifically, a material of the layer 105 was deposited by a resistance-heating method.

The layer 105 contains LiF and has a thickness of 1 nm.

[Tenth Step]

In the tenth step, the electrode 552 was formed over the layer 105. Specifically, materials of the electrode 552 were co-deposited by a resistance-heating method.

The electrode 552 contains Ag and Mg at a volume ratio of Ag:Mg=1:0.1 and has a thickness of 10 nm.

«Operation Characteristics of Device D111»

The operation characteristics of the device D111 were measured at room temperature (see FIG. 14 to FIG. 16). Monochromatic light was emitted in the state where a potential of −4 V relative to the potential of the electrode 551S was supplied to the electrode 552, and the light-to-current conversion efficiency with respect to the amount of irradiation light was measured as EQE (see FIG. 14). Monochromatic light was emitted at intervals of 25 nm in the wavelength range from 375 nm to 750 nm. The potential of the electrode 551S from −6 V to +2 V relative to the potential of the electrode 552 was swept in the state where light with a wavelength of 550 nm was emitted with an intensity of 12.5 µW/cm$^2$, and the density of current flowing through the device was measured (see FIG. 15). In addition, the potential of the electrode 551S from −6 V to +2 V relative to the potential of the electrode 552 was swept in the state where no light was emitted, and the density of dark current flowing through the device was measured (see FIG. 16). Table 5 shows the characteristics of the device D111 and the other devices to be described later.

TABLE 5

| | Layer 114S | y (nm) | EQE @550 nm (%) |
|---|---|---|---|
| Device D111 | Stacked | 10 | 31.66 |
| Device D112 | Stacked | 20 | 13.26 |
| Device D211 | Stacked | 10 | 25.33 |
| Device D212 | Stacked | 20 | 12.30 |
| Device D311 | Mixed | 10 | 16.93 |
| Device D411 | Mixed | 10 | 34.60 |

The device D111 was found to have favorable characteristics. For example, the device D111 has favorable current saturation characteristics and high efficiency. An imaging device also suitable for capturing images of subjects with an analog gray scale was provided.

<Device D112>

The fabricated device D112, which will be described in this example, has a structure similar to that of the photoelectric conversion device 550S (see FIG. 9). The device D112 differs from the device D111 in that the layer 113(1) and the layer 113(2) each have a thickness of 20 nm.

The device D112 was found to have favorable saturation characteristics even in the case where the thickness of the layer 113(2) was large.

<Device D211>

The fabricated device D211, which will be described in this example, has a structure similar to that of the photoelectric conversion device 550S (see FIG. 9).

«Structures of device D211 and device D212»

Table 6 shows the structures of the device D211 and the device D212. Note that y in the table is 10 or 20.

TABLE 6

| Structure | Reference symbol | Material | Composition ratio | Thickness/nm |
|---|---|---|---|---|
| Electrode | 552 | Ag:Mg | 1:0.1 | 10 |
| Layer | 105 | LiF | | 1 |
| Layer | 113 (2) | NBPhen | | y |
| Layer | 113 (1) | 2mDBTBPDBq-II | | y |
| Layer | 114S2 | EtHex-PTCDI | | 30 |
| Layer | 114S1 | Rubrene | | 30 |
| Layer | 112 | BBABnf | | 40 |
| Layer | 104 | BBABnf:OCHD-003 | 1:0.1 | 11 |
| Electrode | 551S | ITSO | | 100 |
| Reflective film | REF | APC | | 100 |

The device D211 differs from the device D111 in that the layer 114S1 has a thickness of 30 nm, not 42 nm, and the layer 114S2 has a thickness of 30 nm, not 18 nm.

The device D211 was found to have favorable saturation characteristics.

<Device D212>

The fabricated device D212, which will be described in this example, has a structure similar to that of the photoelectric conversion device 550S (see FIG. 9). The device D212 differs from the device D211 in that the layer 113(1) and the layer 113(2) each have a thickness of 20 nm.

The device D212 was found to have favorable saturation characteristics even with the thick layer 113(2).

<Device D311>

The fabricated device D311, which will be described in this example, has a structure similar to that of the photoelectric conversion device 550S (see FIG. 10).

«Structure of device D311»

Table 7 shows the structure of the device D311.

TABLE 7

| Structure | Reference symbol | Material | Composition ratio | Thickness/nm |
|---|---|---|---|---|
| Electrode | 552 | Ag:Mg | 1:0.1 | 10 |
| Layer | 105 | LiF | | 1 |
| Layer | 113 (2) | NBPhen | | 10 |
| Layer | 113 (1) | 2mDBTBPDBq-II | | 10 |
| Layer | 114S | Rubrene:EtHex-PTCDI | 0.7:0.3 | 60 |
| Layer | 112 | BBABnf | | 40 |

TABLE 7-continued

| Structure | Reference symbol | Material | Composition ratio | Thickness/nm |
|---|---|---|---|---|
| Layer | 104 | BBABnf:OCHD-003 | 1:0.1 | 11 |
| Electrode | 551S | ITSO | | 100 |
| Reflective film | REF | APC | | 100 |

The device D311 differs from the device D111 in that the layer 114S with a single-layer structure is included instead of a stacked-layer structure in which the layer 114S1 and the layer 114S2 are stacked.

«Fabrication Method for Device D311»

A fabrication method for the device D311 differs from the fabrication method for the device D111 in that materials are co-deposited by a resistance-heating method in the fifth step and the seventh step follows the fifth step, skipping the sixth step.

[Fifth Step]

In the fifth step, the layer 114S was formed over the layer 112. Specifically, materials of the layer 114S were co-deposited by a resistance-heating method.

The layer 114S has a thickness of 60 nm and contains rubrene and EtHex-PTCDI at a weight ratio of rubrene:EtHex-PTCDI=0.7:0.3.

The device D311 was found to have favorable photosensitivity to green light.

<Device D411>

The fabricated device D411, which will be described in this example, has a structure similar to that of the photoelectric conversion device 550S (see FIG. 10).

«Structure of Device D411»

Table 8 shows the structure of the device D411.

TABLE 8

| Structure | Reference symbol | Material | Composition ratio | Thickness/nm |
|---|---|---|---|---|
| Electrode | 552 | Ag:Mg | 1:0.1 | 10 |
| Layer | 105 | LiF | | 1 |
| Layer | 113 (2) | NBPhen | | 10 |
| Layer | 113 (1) | 2mDBTBPDBq-II | | 10 |
| Layer | 114S | Rubrene:EtHex-PTCDI | 0.5:0.5 | 60 |
| Layer | 112 | BBABnf | | 40 |
| Layer | 104 | BBABnf:OCHD-003 | 1:0.1 | 11 |
| Electrode | 551S | ITSO | | 100 |
| Reflective film | REF | APC | | 100 |

The device D411 differs from the device D311 in the composition of the layer 114S.

«Fabrication Method for Device D411»

A fabrication method for the device D411 differs from the fabrication method for the device D111 in that materials are co-deposited by a resistance-heating method in the fifth step and the seventh step follows the fifth step, skipping the sixth step.

[Fifth Step]

In the fifth step, the layer 114S was formed over the layer 112. Specifically, materials of the layer 114S were co-deposited by a resistance-heating method.

The layer 114S has a thickness of 60 nm and contains rubrene and EtHex-PTCDI at a weight ratio of rubrene:EtHex-PTCDI=0.5:0.5.

The device D411 was found to have favorable photosensitivity to green light. This application is based on Japanese Patent Application Serial No. 2021-077640 filed with Japan Patent Office on Apr. 30, 2021 and Japanese Patent Application Serial No. 2021-094340 filed with Japan Patent Office on Jun. 4, 2021, the entire contents of which are hereby incorporated by reference.

What is claimed is:

1. A photoelectric conversion device comprising:
a first electrode;
a second electrode; and
a first unit,
wherein the first unit is located between the first electrode and the second electrode,
wherein the first unit contains a first electron-donating material and a first electron-accepting material,
wherein the first electron-donating material is a condensed aromatic compound,
wherein the first electron-accepting material has a perylene skeleton and two or more alkyl groups, and
wherein the alkyl groups each independently have carbon atoms whose number is greater than or equal to 1 and less than or equal to 13.

2. The photoelectric conversion device according to claim 1,
wherein the first unit exhibits a local maximum at a wavelength of less than 500 nm and an absorption edge at a wavelength of greater than or equal to 500 nm in an absorption spectrum.

3. The photoelectric conversion device according to claim 1,
wherein the first electron-donating material is a condensed aromatic compound having condensed rings whose number is greater than or equal to 4 and less than or equal to 11.

4. The photoelectric conversion device according to claim 1,
wherein the alkyl groups each have a branched structure.

5. The photoelectric conversion device according to claim 1,
wherein the first electron-accepting material is a perylenetetracarboxylic diimide derivative expressed by General Formula (R0),

[Chemical Formula 1]

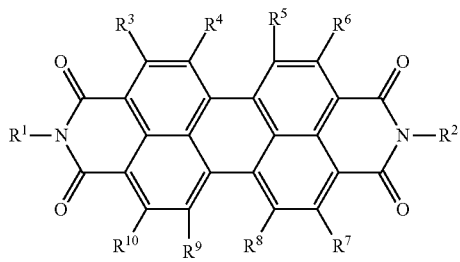

(R0)

wherein:
$R^1$ and $R^2$ each independently represent hydrogen, a chain alkyl group having 1 to 13 carbon atoms, or a branched alkyl group having 3 to 13 carbon atoms, and
$R^3$ to $R^{10}$ each independently represent hydrogen, a chain alkyl group having 1 to 13 carbon atoms, a branched alkyl group having 3 to 13 carbon atoms, a halogenated alkyl group having 1 to 13 carbon atoms, a cycloalkyl group having 3 to 13 carbon atoms, or halogen.

6. The photoelectric conversion device according to claim 1, further comprising a first layer,
wherein the first layer is located between the first electrode and the first unit,
wherein the first layer contains a second electron-accepting material, and
wherein the first layer has an electrical resistivity greater than or equal to $1 \times 10^2$ Ω·cm and less than or equal to $1 \times 10^8$ Ω·cm.

7. The photoelectric conversion device according to claim 1, further comprising a second layer,
wherein the second layer is located between the first unit and the second electrode, and
wherein the second layer contains a second electron-donating material.

8. The photoelectric conversion device according to claim 1,
wherein the first unit includes a third layer, a fourth layer, and a fifth layer,
wherein the third layer is located between the fourth layer and the fifth layer,
wherein the third layer contains the first electron-accepting material and the first electron-donating material,
wherein the fourth layer is located between the first electrode and the third layer,
wherein the fifth layer is located between the third layer and the second electrode,
wherein the fourth layer contains a hole-transport material, and
wherein the fifth layer contains an electron-transport material.

9. An optical functional device comprising:
the photoelectric conversion device according to claim 8; and
a light-emitting device,
wherein the light-emitting device is adjacent to the photoelectric conversion device,
wherein the light-emitting device includes a second unit, a third electrode, and the second electrode,
wherein the second unit is located between the third electrode and the second electrode,
wherein the second unit includes a sixth layer, the fourth layer, and the fifth layer,
wherein the fourth layer is located between the third electrode and the sixth layer,
wherein the fifth layer is located between the sixth layer and the second electrode, and
wherein the sixth layer includes a light-emitting material.

10. An optical functional device comprising:
the photoelectric conversion device according to claim 1; and
a light-emitting device,
wherein the light-emitting device is adjacent to the photoelectric conversion device.

11. A photoelectric conversion device comprising:
a first electrode;
a second electrode; and
a first unit,
wherein the first unit is located between the first electrode and the second electrode,
wherein the first unit contains a first electron-donating material and a first electron-accepting material,
wherein the first electron-donating material is a condensed aromatic compound,
wherein the first electron-accepting material has a perylene skeleton and two or more alkyl groups, wherein the alkyl groups each independently have carbon atoms whose number is greater than or equal to 1 and less than or equal to 13, and wherein the alkyl groups each have a branched structure.

12. The photoelectric conversion device according to claim 11, wherein the first unit exhibits a local maximum at a wavelength of less than 500 nm and an absorption edge at a wavelength of greater than or equal to 500 nm in an absorption spectrum.

13. The photoelectric conversion device according to claim 11, wherein the first electron-donating material is a condensed aromatic compound having condensed rings whose number is greater than or equal to 4 and less than or equal to 11.

14. The photoelectric conversion device according to claim 11, wherein the first electron-accepting material is a perylenetetracarboxylic diimide derivative expressed by General Formula (R0),

[Chemical Formula 1]

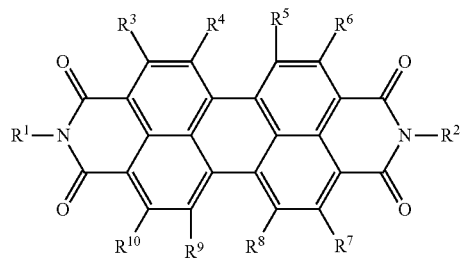

(R0)

wherein:

$R^1$ and $R^2$ each independently represent hydrogen, a chain alkyl group having 1 to 13 carbon atoms, or a branched alkyl group having 3 to 13 carbon atoms, and $R^3$ to $R^{10}$ each independently represent hydrogen, a chain alkyl group having 1 to 13 carbon atoms, a branched alkyl group having 3 to 13 carbon atoms, a halogenated alkyl group having 1 to 13 carbon atoms, a cycloalkyl group having 3 to 13 carbon atoms, or halogen.

15. The photoelectric conversion device according to claim 11, further comprising a first layer, wherein the first layer is located between the first electrode and the first unit, wherein the first layer contains a second electron-accepting material, and wherein the first layer has an electrical resistivity greater than or equal to $1\times10^2$ Ω·cm and less than or equal to $1\times10^8$ Ω·cm.

16. The photoelectric conversion device according to claim 11, further comprising a second layer, wherein the second layer is located between the first unit and the second electrode, and wherein the second layer contains a second electron-donating material.

17. The photoelectric conversion device according to claim 11, wherein the first unit includes a third layer, a fourth layer, and a fifth layer, wherein the third layer is located between the fourth layer and the fifth layer, wherein the third layer contains the first electron-accepting material and the first electron-donating material, wherein the fourth layer is located between the first electrode and the third layer, wherein the fifth layer is located between the third layer and the second electrode, wherein the fourth layer contains a hole-transport material, and wherein the fifth layer contains an electron-transport material.

18. An optical functional device comprising:

the photoelectric conversion device according to claim 17; and a light-emitting device, wherein the light-emitting device is adjacent to the photoelectric conversion device, wherein the light-emitting device includes a second unit, a third electrode, and the second electrode, wherein the second unit is located between the third electrode and the second electrode, wherein the second unit includes a sixth layer, the fourth layer, and the fifth layer, wherein the fourth layer is located between the third electrode and the sixth layer, wherein the fifth layer is located between the sixth layer and the second electrode, and wherein the sixth layer includes a light-emitting material.

19. An optical functional device comprising:

the photoelectric conversion device according to claim 11; and a light-emitting device, wherein the light-emitting device is adjacent to the photoelectric conversion device.

* * * * *